(12) United States Patent
Creighton et al.

(10) Patent No.: US 8,491,514 B2
(45) Date of Patent: Jul. 23, 2013

(54) CUSTOMIZABLE THERAPEUTIC COMPRESSION GARMENT AND METHOD

(75) Inventors: Barry L. Creighton, College Station, TX (US); Wade P. Farrow, College Station, TX (US)

(73) Assignee: Farrow Medical Innovations Holdings LLC, Bryan, TX (US)

( * ) Notice: Subject to any disclaimer, the term of this patent is extended or adjusted under 35 U.S.C. 154(b) by 361 days.

(21) Appl. No.: 12/796,579

(22) Filed: Jun. 8, 2010

(65) Prior Publication Data

US 2010/0312160 A1    Dec. 9, 2010

Related U.S. Application Data

(60) Provisional application No. 61/185,129, filed on Jun. 8, 2009.

(51) Int. Cl.
*A61F 13/06* (2006.01)

(52) U.S. Cl.
USPC .................................. 602/60; 602/63; 602/75

(58) Field of Classification Search
USPC .................................. 602/60–63, 75, 20–27
See application file for complete search history.

(56) References Cited

U.S. PATENT DOCUMENTS

| | | | |
|---|---|---|---|
| 2,687,723 A | 8/1954 | Stern | |
| 2,816,361 A | 12/1957 | Jobst | |
| 3,298,366 A | 1/1967 | Moore et al. | |
| 3,312,219 A | 4/1967 | Peckham | |
| 3,856,008 A | 12/1974 | Fowler et al. | |
| 4,215,687 A | 8/1980 | Shaw | |
| 4,577,622 A | 3/1986 | Jennings | |
| 4,756,026 A | 7/1988 | Pierce, Jr. | |
| 5,036,838 A | 8/1991 | Sherman | |
| 5,218,954 A | 6/1993 | van Bremmelen | |
| 5,387,183 A | 2/1995 | Jones | |
| 5,520,630 A | 5/1996 | Daneshvar | |
| 5,653,244 A | 8/1997 | Shaw | |
| 5,897,518 A | 4/1999 | Shaw | |
| 5,918,602 A | 7/1999 | Shaw et al. | |
| 5,993,405 A | 11/1999 | Wynn | |
| 6,032,300 A | 3/2000 | Bainbridge et al. | |
| 6,109,267 A | 8/2000 | Shaw et al. | |
| 6,152,893 A | 11/2000 | Pigg et al. | |
| 6,254,554 B1 | 7/2001 | Turtzo | |

(Continued)

FOREIGN PATENT DOCUMENTS

| | | |
|---|---|---|
| GB | 2373444 | 9/2002 |
| WO | WO 99/36019 | 7/1999 |

(Continued)

OTHER PUBLICATIONS

Hawkins, A New Cohesive Short-Stretch Bandage and Its Application, British Journal of Nursing, Feb. 22, 2001-Mar. 7, 2001, pp. 249-253.

(Continued)

*Primary Examiner* — Michael A. Brown
(74) *Attorney, Agent, or Firm* — Pate Peterson, PLLC; Warren M. Pate

(57) ABSTRACT

Provided is a therapeutic compression apparatus that includes a compression material. In one example, the apparatus includes a large surface area of a single sheet of compression material. The apparatus may include indicia that allow it to be trimmed to fit a patient.

23 Claims, 22 Drawing Sheets

U.S. PATENT DOCUMENTS

| | | | |
|---|---|---|---|
| 6,338,723 B1 * | 1/2002 | Carpenter et al. | 602/75 |
| 6,361,397 B1 * | 3/2002 | Mankovitz et al. | 450/20 |
| 6,415,525 B1 | 7/2002 | Watkins | |
| 6,573,419 B2 | 6/2003 | Naimer | |
| 6,613,007 B1 | 9/2003 | Reid, Jr. | |
| 6,617,485 B2 | 9/2003 | Herzberg | |
| 6,852,089 B2 | 2/2005 | Kloecker et al. | |
| 6,860,862 B2 | 3/2005 | Waldridge et al. | |
| 7,112,183 B2 | 9/2006 | Binder et al. | |
| 7,135,007 B2 * | 11/2006 | Scott et al. | 602/75 |
| 7,173,161 B1 | 2/2007 | Kandt | |
| 7,329,232 B2 * | 2/2008 | Lipshaw et al. | 602/61 |
| 7,513,881 B1 | 4/2009 | Grim et al. | |
| 7,867,185 B2 | 1/2011 | Lipshaw | |
| 7,942,838 B2 | 5/2011 | Farrow | |
| 2003/0149389 A1 | 8/2003 | Daneshvar | |
| 2003/0167548 A1 | 9/2003 | LaShoto et al. | |
| 2004/0122344 A1 | 6/2004 | Nelson et al. | |
| 2005/0113729 A1 | 5/2005 | Scott et al. | |
| 2005/0192524 A1 | 9/2005 | Lipshaw et al. | |
| 2005/0209545 A1 | 9/2005 | Farrow et al. | |
| 2006/0010574 A1 | 1/2006 | Linnane et al. | |
| 2007/0179421 A1 | 8/2007 | Farrow | |
| 2007/0276310 A1 | 11/2007 | Lipshaw et al. | |
| 2007/0282232 A1 | 12/2007 | Hoffman | |
| 2010/0056973 A1 | 3/2010 | Farrow et al. | |
| 2011/0087145 A1 | 4/2011 | Farrow et al. | |
| 2011/0257575 A1 | 10/2011 | Farrow et al. | |
| 2012/0010551 A1 | 1/2012 | Farrow et al. | |

FOREIGN PATENT DOCUMENTS

| | | |
|---|---|---|
| WO | WO 00/15139 | 3/2000 |
| WO | WO 2005/092401 | 10/2005 |
| WO | WO 2008/127929 | 10/2008 |
| WO | WO 2010/025186 | 3/2010 |
| WO | WO 2010/144492 | 12/2010 |
| WO | WO 2011/044500 | 4/2011 |

OTHER PUBLICATIONS

Lawrance, Use of Velcro Wrap System in the Management of Lower Limb Lymphoedema/Chronic Oedema, Journal of Lymphoedema, 2008, vol. 3, No. 2, pp. 65-70.

Mayrovitz, Compression Therapy: A Summary of Important Concepts and Features, 2004, pp. 1-11.

Medassist Orthotic Products, www.medassistgp.com, 6 pages.

Mosti et al., Compression Therapy in the Treatment of Leg Ulcers, Acia Vulnologica, vol. 7, No. 3, May 2009, pp. 1-20.

Thomas et al., An Evaluation of a New Type of Compression Bandaging System, World Wide Wounds, Sep. 2003, pp. 1-15.

Trinity Lymphedema Centers, http://www.trinitylc.com/cmpgarm1.html, 3 pages.

Understanding Compression Therapy, Medical Education Partnership, LTD, 2003, pp. 1-17.

PCT: International Search Report and Written Opinion of PCT/US2010/037828 (counter part application); Nov. 9, 2010; 10 pages.

3M Coban 2 Layer Compression System, Commonly Asked Questions, Feb. 13, 2007, pp. 1-3.

3M Coban 2 Layer Compression System, Patient Instructions, 2006, 1 page.

New 3M Coban 2 Layer Compression System Introduced for the Treatment of Edema Associated with Venous Leg Ulcers, Press Release, May 1, 2006, pp. 1-3.

Farbifoam Achilles Healer, http://www.fabrifoam.com/p-achilleshealer.html, retrieved Sep. 30, 2005.

Fabrifoam AnkleGard, http://www.fabrifoam.com/p-anklegard.html, retrieved Sep. 30, 2005.

Fabrifoam AnkleWrap, http://www.fabrifoam.com/p-anklewrap.html, retrieved Sep. 30, 2005.

Fabrifoam CarpalGard, http://www.fabrifoam.com/p-carpalgard.html, retrieved Jan. 7, 2010.

Fabrifoam ElbowGard, http://www.fabrifoam.com/p-elbowgard.html, retrieved Jan. 7, 2010.

Fabrifoam KneeGard, http://www.fabrifoam.com/p-kneegard.html, retrieved Sep. 30, 2005.

Fabrifoam MediWrap, http://www.fabrifoam.com/p-mediwrap.html, retrieved Jan. 7, 2010.

Fabrifoam NustimWrap, http://www.fabrifoam.com/p-nustimwrap.html, retrieved Sep. 30, 2005.

Fabrifoam PattStrap, http://www.fabrifoam.com/p-pattstrap.html, retrieved Jan. 7, 2010.

Fabrifoam ProWrap, http://www.fabrifoam.com/p-prowrap.html, retrieved Sep. 30, 2005.

Fabrifoam PSC, http://www.fabrifoam.com/p-psc.html, retrieved Sep. 30, 2005.

Fabrifoam SuperWrap, http://www.fabrifoam.com/p-superwrap.html, retrieved Sep. 30, 2005.

Fabrifoam WristWrap, http://www.fabrifoam.com/p-wristwrap.html, retrieved Jan. 7, 2010.

* cited by examiner

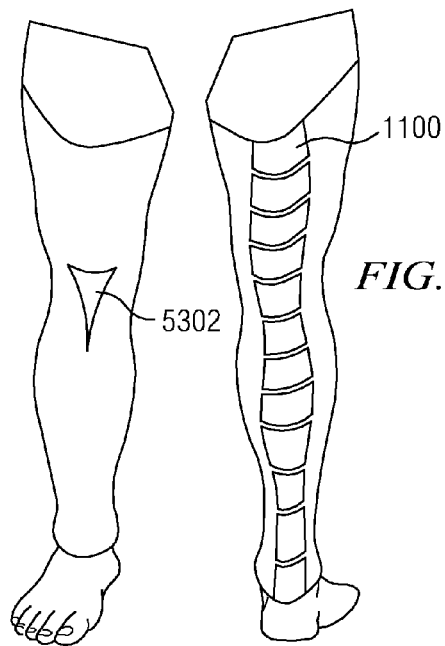
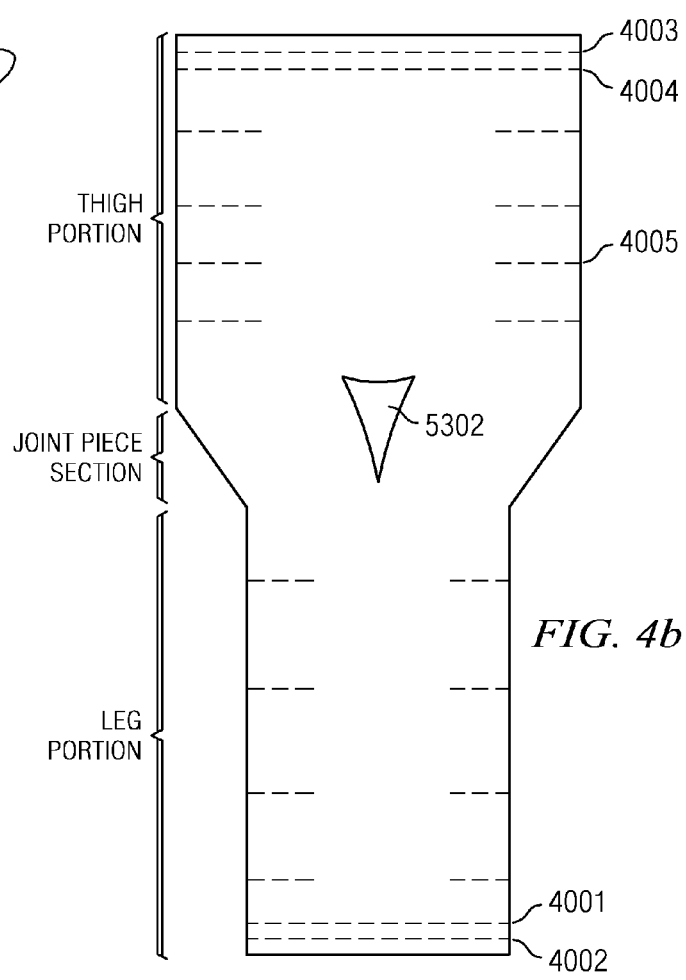
FIG. 4a
FIG. 4b

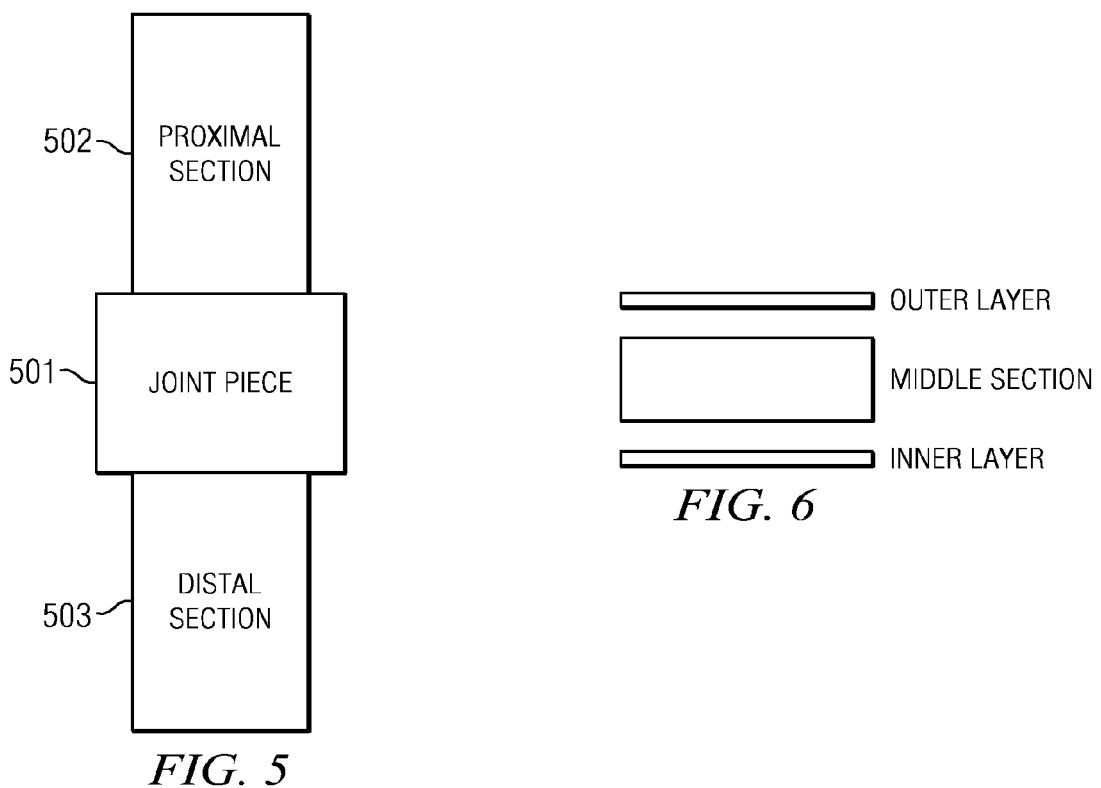
*FIG. 5*
*FIG. 6*
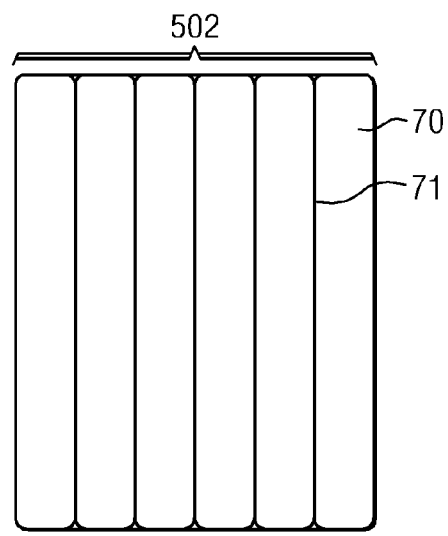
*FIG. 7*

CUSTOMIZABLE THERAPEUTIC COMPRESSION GARMENT AND METHOD

CROSS-REFERENCE TO RELATED APPLICATIONS

This application claims the benefit of U.S. Provisional Application Ser. No. 61/185,129, filed on Jun. 8, 2009, and entitled CUSTOMIZABLE THERAPEUTIC COMPRESSION GARMENT AND METHOD.

U.S. Provisional Application Ser. No. 61/185,129, filed on Jun. 8, 2009, and entitled CUSTOMIZABLE THERAPEUTIC COMPRESSION GARMENT AND METHOD is incorporated herein.

TECHNICAL FIELD

This disclosure relates to apparatus, methods, and systems for treating medical conditions by application of therapeutic compression to general and specific areas of a patient's or animal's body.

BACKGROUND OF THE INVENTION

Limbs have very complex shapes. They are not cylindrical or regularly shaped in any sense. Therefore, fitting a limb with a compression garment that is made from a single piece of material presents special design problems that must be addressed to fit complex limb curvatures with what is basically a single piece of planar material. If limbs were cylindrical, then bending a planar shape around a cylindrical limb would present no particular problem because a plane will readily bend around a cylinder and even a conical volume. However, limbs have complex shapes with varying complex curvatures. These shapes may hereinafter be referred to as limb hulls. The problem of fitting a planar piece of material around a limb hull may be analogous to wrapping a sheet of paper around an apple. Even though an apple has a much simpler curvature shape than a limb, one can immediately see that a planar sheet of paper would have to be altered significantly in order to fit neatly around the apple.

The challenge of fitting a limb neatly with a planar sheet is only one part of the design problem. A therapeutic compression garment must also be designed so that proper compression levels and compression gradients are provided for each area of an affected limb. Another important aspect related to compression is to design the compression garment such that the proper compression levels and compression gradients are directed at the limb in a desired direction (hereinafter, a compression magnitude with a compression direction is called a compression vector). Therefore, the single piece compression garment must have the properties of good fit and proper therapeutic compression levels and compression vectors.

A further challenge related to the design of a single piece compression garment is patient comfort. A planar piece of material may be cut to provide a good fit and proper compression, but if it results in patient discomfort due to pinching, buckling, or other reasons, the patient is unlikely to be compliant in wearing the compression garment and may not benefit from the therapy.

Another aspect of an effective single piece compression garment is that it should have good structural integrity. For example, if a compression garment made from a single piece of material has many lengthy cuts so that a good fit may be achieved, it may have little structural integrity and may be unwieldy to use. For a single piece compression garment to have high structural integrity, it is important to design it such that each cut is carefully planned so as to minimize the number of cuts, thereby making a compression garment that feels whole and is easy to use.

The use of properly fitting compression garments is important in treating various conditions. For example, excessive interstitial fluid accumulation, referred to as edema, may arise from a variety of illnesses and conditions, including venous valvular insufficiency, postphlebotic syndrome, posttraumatic swelling, postoperative swelling, congestive heart failure related swelling, hypoalbuminemia related swelling, drug related swelling, and lymphedema. Compression apparatus method and systems control edema by reduction of interstitial fluids which increases nutrient delivery to tissues, removes waste from tissues, relieves pain from swelling, and decreases risk of infection. However, prior-art compression technologies have certain drawbacks as explained below.

Wounds complicate the problem because traditional compression apparatus may restrict drainage of fluid from sores, cause skin breaks and/or ulcerations, and may promote wound breakdown and increased risk of blood clot formation in the veins.

Clinically, certain patient populations develop pressure necrosis to underlying skin and tissue breakdown occasionally occurs with traditional modalities, including compression stockings. This occurs most commonly over the anterior ankle where the tibialis tendon can be very prominent in some individuals. Some patients have a tibia which is prominent and plough-shaped, such that these patients can experience breakdown across parts of the shin area under these garments. Similarly, the malleoli and metatarsal heads of the 1st and 5th digits are occasional problems as well.

Some patients have troublesome anatomical morphologies, such as large bunions, metatarsal head protrusions, or accentuated ankle malleoli, which are predisposed to higher peak compression levels. Some patients requiring compression have fragile skin that cannot tolerate even moderately elevated compressive or shear forces. Patients with lymphedema and venous insufficiency often develop fibrotic areas within the tissues or may be lacking in lymphatic integrity.

Many of the above mentioned patients are prone to bacterial and fungal skin infections, all of which can be life threatening.

Particularly problematic in venous and lymphedema patients and other patients requiring long term compression is the incidence of dermatitis, causing itching, and discomfort which contribute to lack of compliance with compression and is therefore also detrimental to attempts at edema reduction and healing of wounds in edematous limbs.

Because of considerable variation in limb shapes and sizes, custom garments may traditionally be required. However, conventional custom garments take time to manufacture. It is not uncommon, for instance, for conventional custom compression stockings to take one month from date of order until the patient receives the garment. Furthermore, errors in manufacturing and measurement sometimes necessitate remanufacturing the garment or altering the garment in order to get a proper fit. This is very inconvenient for the patient, who needs therapeutic compression immediately, and must make-do with an off-the-shelf garment or bandage until the custom garment arrives and fits correctly.

RELATED ART

Many devices can be used for treatment of edema, swelling, or venous ulcerations. For example, the Unna boot, invented by German dermatologist Dr. Unna in the late 1800's for use in the treatment of venous ulcerations, uses a zinc paste bandage which dries to form an inelastic shell around the limb. When a calf muscle expands on activation the muscle cannot expand against this rigid shell. Thus high subbandage pressure redirects the pressure inward where it exerts force on the deep venous system, augmenting venous return. While useful in some applications, the Unna boot is subject to a number of limitations. For example, it is applied as a rigid shell. Therefore, controlled baseline compression is difficult to ascertain because there is no feedback to guide when appropriate compression levels are obtained. Furthermore, as edema reduces, the boot loses compression and allows bandages to shift, possibly increasing drainage in the case of any wounds present. A further limitation is that the rigid shell boot can cause pressure ulceration if it dries with too much pressure over bony prominences or other sensitive tissue areas. Patients undergoing total contact cast therapy are commonly unable to feel when a rigid cast is not properly applied causing dangerous pressure points or when padding is insufficient, exposing the skin to the rough inner surface of the cast.

Circaid and LegAssist have produced nonelastic garments for treatment of swelling, basically recreating a removable nonelastic garment with performance similar to the Unna boot. There are limitations to these type garments. The garment does not form fit well as it is relatively nonelastic. The garment loosens as edema reduces, and requires more frequent readjustments, and inelastic products do not function well over joints. Finally, there is no intuitive way that a user can control the baseline or resting compression as there is no feedback from the garment.

Some products use layers of long and mid-stretch bandages in combination to create a flexible shell which has some elasticity, provides padding to the skin, and can apply fairly uniform compression. A four layer compression system invented in the 1980s by Dr. Christine Moffatt is a single use disposable bandage system. Multilayer compression systems are now available in 2 to 4 layers by many companies. However, properly trained and experienced health care practitioners are required for application of these systems to insure controlled compression and to effect safe distal to proximal compression gradients.

The Coban 2 layer bandage system is such a system with a single use disposable bandage. This garment shows promise in treatment of oedemas, due to lower profile and studies showing decreased slippage over a one week period. The garment can be applied at less than maximal stretch (ex. Applied at 50% or 75% of possible maximal stretch—i.e. 50% of maximal stretch in this case means bandage applied at 15% stretch) to reduce compression level. The system features an inner layer with a thin layer of foam with a layer of cohesive bandage and very little compression, and an outer layer with approximately 30% maximum stretch (bandage stretches 130% original length) which is designed to provide therapeutic compression. The system is lower profile than multilayer bandages, and many users feel it allows them to have easier ambulation and lower profile under pants as well. The foam under layer is considered padding and helps reduce slippage, but is also applied over the entire limb. The Coban 2 layer compression bandage system, however, sometimes does not provide adequate padding to certain problems areas, and extra padding must be used or tissue breakdown can result.

Padding can also be useful to help reduce swelling in problem areas. This is seen for example in the retromalleolar area, which can be difficult to contain with compression garments or bandages without additional padding to help press in and increase interstitial pressures, effectively augmenting return of fluid to the capillaries and lymphatics. Therefore, padding under compression garments may prevent trauma to underlying tissues.

For lymphedema patients, solid and chipped foam liners for padding are known in the art. These are sold under the name Circaid Silhouette, Jovi, Solaris and others. Higher quality liners use specific foam densities to provide better padding and protection of underlying tissues. Some liners may contain channeling, which is felt by many experts to help channel flow of lymph fluid by utilizing areas of higher compression and areas of lower compression.

Most current solutions provide chipped foam sewn into a sleeve with channeling. These products are thick, and some patients complain they are hot and bulky to wear on a day in and day out basis. These solutions are expensive, and are mainly used for treatment of lymphedema and fibrotic tissue caused by lipodermatosclerosis, for which many experts find these products useful. Additionally, the excess bulk means that regular pants often cannot be worn over such garments, and if worn over a joint tend to restrict the motion in that joint. Because of these limitations, such garments are typically worn at night and most patients do not use them for everyday use. Other solutions include smooth foam liners, however, these also suffer from being very insulative and bulky, not to mention expensive because the foam is applied throughout the liner.

Conventional compression bandages that employ short-stretch material or that have short-stretch properties are advantageous because they allow prescribers to properly dictate the level of resting compression best suited for the patient. However, these bandages must be applied by a practitioner who has been properly trained and practiced in the amount of tension they should use during application. Otherwise the patient may be harmed by resulting circulation problems if the bandages are applied with too much tension.

In light of the foregoing, there is a need in the art for compression apparatus, methods and systems that solve these and other issues in the prior art.

SUMMARY OF THE INVENTION

In accordance with aspects of the present invention, provided is a compression garment with planar construction, which may include padding. This garment may employ trim-to-fit indicia and markings to properly trim the garment.

BRIEF DESCRIPTION OF THE DRAWINGS

The present invention is described with reference to the accompanying drawings.

FIG. 4a is an illustration of a compression garment applied to a leg and thigh.

FIG. 4b is an illustration of the compression garment of 4a prior to trimming and fitting.

FIG. 5 is a diagram of a compression garment with joint piece and distal and proximal portions.

FIG. 6 is a cross section of the compression material.

FIG. 7 is an is an illustration of channeled padding.

FIGS. 29*a-d* are illustrations of embodiments of a Choice Algorithm.

DETAILED DESCRIPTION

Figure 1A:
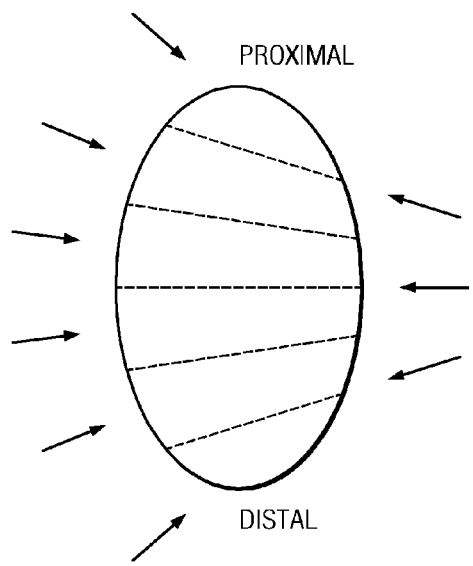
FIGS. 1a and 1b are illustrations of compression vectors to a spherical shape.

The present disclosure relates generally to compression treatments for conditions such as edema and, more specifically, to a compression garment to be used under a device for applying compressive pressure to a person's body in order to facilitate reduction of interstitial fluids from a body trunk and/or limb extremity and to provide support and fatigue relief.

It is to be understood that the present disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not, in itself, dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 2A:
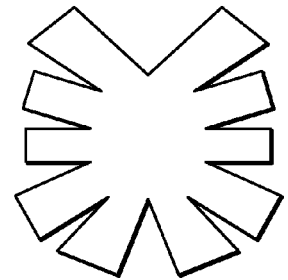
FIGS. 2a and 2b are illustrations of compression garments to provide compression to a spherical shape.
Figure 1B:
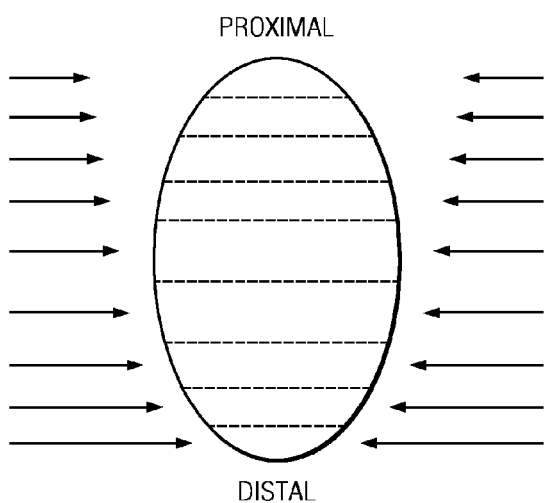
Figure 2B:
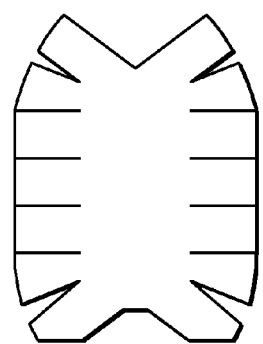

Referring to the compression vectors of FIGS. 1*a* and 1*b*, the ovals represent simplified model volumes of a limb portion. The areas on the ovals separated by the dotted lines represent areas of the limb experiencing levels of compression. It is noted that these simplified models show only regular convex portions. However, an actual limb frequently includes concave portions, irregular convex portions, cylindrical portions, and other geometries where a compression garment may be needed to generate compression vectors having varying compression levels and orientations to accommodate a particular therapy. The areas on the two ovals show two possible configurations for a compression garment design and the resulting compression vectors, as shown in FIGS. 2*a* and 2*b*. The bottom figure shows radial compression while the top figure shows a hybrid compression comprising both radial and axial components. Although these two examples show radial and hybrid compression, a compression garment may be designed for radial compression, hybrid compression, any combinations of these compression types, and/or compression in any other vector orientations that may be suitable for a specific type of therapy. Also to be noted in the figures is that the magnitudes of the compression vectors are highest distally and are progressively reduced proximally. The example ovals also illustrate graphically that a compression garment may need to have cuts that are geometrically unique to each configuration.

By varying the width of each cut, the compression levels can be altered. For instance, if a distal band is one half (½) the width of a more proximal band, and the user pulls the narrower band with same force thereby generating higher tension, the garment will have twice the compression per surface area on the more narrow (distal) band. Thus, by changing the materials selected and the characteristics of the cuts, a garment can be designed to provide varying levels of compression at different limb levels. This is important because it allows the garment to be designed to provide more customized therapeutic compression. For instance, more narrow cuts could be used distally to provide increased compression, and wider cuts could be made more proximally. This would allow more compression vectors distally than proximally and create graduated compression. Additionally, for an edematous lobule, it may be desirable to lift and compress the lobule. The cuts and compression vectors of the design may take a more upward radial component to effectively lift and compress the lobule to decompress its edema.

This disclosure details a compression garment with optional embodiments composing padding over prominent bony areas. This garment is designed to be very low profile and breathable. The garment is manufactured based upon using a large planar piece of compression material. In the preferred embodiment, this compression material is short-stretch material and also trimmable. The garment is applied at or near the end-stretch of the material to provide a therapeutic resting compression level. Additionally, in the preferred embodiment, the garment is unique in design in that it is trimmable. This allows the garment to be modified at the point of sale or point of fitting for the patient. The patient can thus receive a customized garment quickly, without having to wait for it to be ordered and delivered. Since the customizable design fits a very wide range of sizes, the trim-to-fit design requires much less inventory since fewer sizes need to be stocked. Furthermore, the patient can use the garment for acute treatment phase of edema reduction. As the patient's edema reduces, the garment can be further trimmed as necessary to fit properly, without excess overlapping. The garment can furthermore be used for maintenance phase of treatment to prevent reulceration of venous ulcers or prevent reaccumulation of the edema. The garment design is ideal for postsurgical and outpatient wound care use, as one garment would fit over 90% of all patients and can be quickly customized to fit exactly to the patient and only a small number of sizes or single size would need to be stocked in the hospital or clinic. Using few sizes would help ensure correct stocked levels as fewer sizes would need to be stocked, provide proper compression to a wide range of patients, require smaller footspace for less storage space, and reduce cost of inventory for clinics and hospitals.

An additional benefit of some embodiments of the invention is the low profile padding technology which is important, as it allows higher resting levels of compression to be used safely by decreasing skin surface pressure to bony areas by padding these areas, while maintaining lower profile and higher breathability to areas that do not need this padding. The Sub-Bandage Pressure is the pressure exerted just under the garment. In the absence of padding, the Skin Surface Pressure is same as the subbandage pressure. The more padding there is between the compression bandage and the skin, the lower the skin surface compression. Thus, a garment incorporating padding reduces skin surface pressure by lowering the pressure over the bony/tendinous area low enough that capillary perfusion pressure is not compromised. Compromising capillary perfusion pressure would result in tissue areas which were not adequately perfused and lead to tissue ischemic damage and tissue loss.

In some embodiments, the padding would comprise of one or more layers of circular spacer fabric. This fabric has two layers of fabric with mostly air in-between and held in place by the orientation of threads between the fabric layers and is created on a circular knit machine. Such technology is emerging now, and available from Beverly Knits Inc. in Charlotte, N.C. and its construction is detailed in U.S. Pat. No. 6,755, 052. Other manufacturers of spacer fabric include 3 Mesh by Mueller Textiles of Wiehl, Germany; Spacetec by Heathcoat Fabrics Ltd, Devon, UK; AirX by Tytex, Ikast, Denmark; XD Spacer Fabric by Changshu Jianhua Knitting Company, Jiangsu, China; XD Spacer Fabric by Baltex, Derbyshire, UK; or WellCool Cushion Technology Co, Ltd of Quanzhou, Fujian, China. The spacer fabric is highly breathable, as the monofilaments between layers allow air to be used with no foam, neoprene, or breathoprene. The result is a lighter and safer compression garment.

Different types of spacer fabric may be used with a variety of fibers, filaments or monofilaments between layers, and various densities of fibers, and length of fibers depending on application. For instance more compression resistance is better for fibrotic tissue. Other examples may include thicker padding under tighter compression over certain body parts like the tibialis tendon which varies in prominence. Depending on the application varying stretch of fabric layer(s) may be needed depending on garment design.

Figure 8:
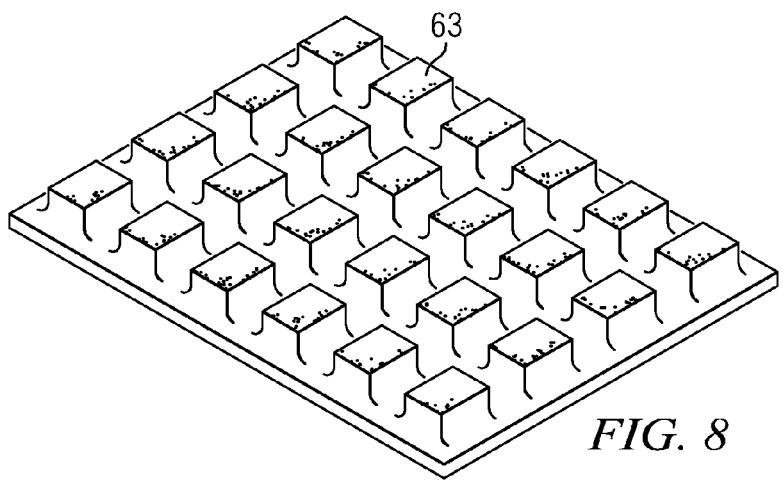
FIG. 8 is an illustration of waffled padding.
Figure 9:
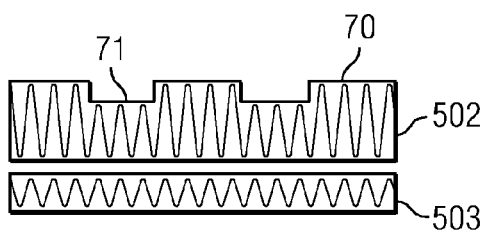
FIG. 9 is an illustration of a second embodiment of waffled padding.
Figure 10:
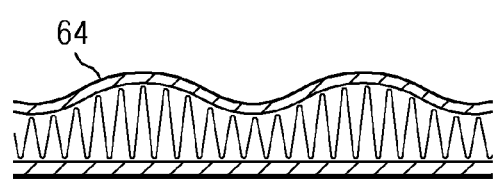
FIG. 10 is an illustration of a third embodiment of waffled padding.
Figure 20:
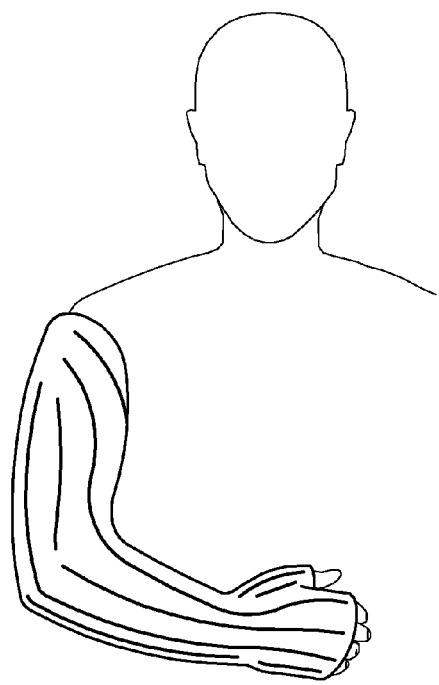
FIGS. 20 and 21 are illustrations of the compression garment showing the garment's directional channeled padding to augment lymphatic return.
Figure 21:
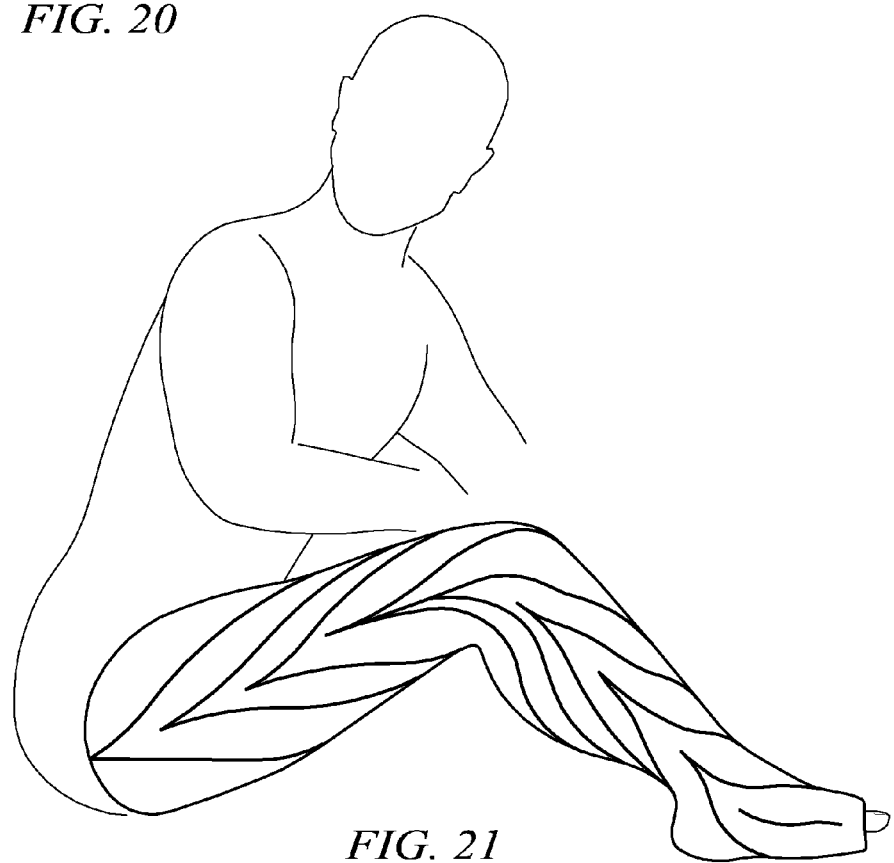

In some embodiments, the spacer fabric would be knit on a programmable or computer programmable circular knit machine, with spacer fabric only in designated areas, and in other areas single layer or two layers of spacer fabric may be used in the garment. Using this approach, sheets of spacer fabric can be manufactured with channels (FIG. 7), or waffled padding (FIG. 8). The channeling may be accomplished with abrupt raised areas 70 and recessed areas 71 as shown in 502 of FIG. 9. In FIG. 9, there is optional additional padded layer 503. In other embodiments, the channeling is subtle as shown in FIG. 10. Alternatively, the spacer fabric can be made with channeled patterns that mimic the lymphatic return of the skin, helping to redirect lymph flow more proximally (FIGS. 20 and 21). FIG. 20 shows the channeled padding for an arm garment and FIG. 21 shows the channeled padding for a leg garment.

The spacer fabric has many interesting applications for use as an alternative to foam. Because it is highly breathable but has compression resistance, it may be superior to foam for use as padding under compression garments. The higher breathability means less skin moisture, which decreases incidence of dermatitis and decrease risk of fungal infection. This is particularly important in lymphedema patients and patients requiring long term compression, where the incidence of dermatitis, itching, and discomfort contributes to lack of compliance with compression in patients and is therefore also detrimental to attempts at edema reduction and healing of wounds in edematous limbs.

Alternative materials to spacer fabric include open cell foam, closed cell foam, viscoelastic foam, fluid filled elastic enclosed padding, silicon padding, terry cloth, wadded fabric, flexible aerogel blanket, or injected foam (single or chipped foam or multipart foam).

As discussed above, the padded regions of the planar garment may be formed by incorporating a padding material formed of a spacer fabric therein. Conventional padding materials, typically comprising foam, gel, or other padding materials provide only limited breathability, sometimes resulting in heat rash dermatitis, fungal infection, itching, and overall patient discomfort. This can also result in lack of patient compliance when such garments are used and prescribed. In short, this problem with conventional materials can be detrimental to attempts at edema reduction and healing of wounds in edematous limbs.

However, exchanging conventional padding materials with spacer materials eliminates many of the shortcoming of the conventional materials. As stated above, spacer material comprises a layered fabric material formed of at least two layers of materials separated by threads or filaments extending from one layer to the other to compressably maintain the spacing in a way that provides cushioning to loading on one of the layers. Because the spacer fabric has mostly air in-between the two layers, the material is highly breathable. Furthermore, the layers also may be highly breathable. This higher breathability means less incidence of heat rash dermatitis and less risk fungal infection. This reduction in the incidence of dermatitis, itching, and overall patient discomfort directly addresses issues contributing to lack of compliance with compression in patients. Accordingly, incorporating spacer fabric as a padding material would increase patient compliance, directly affecting and improving the results of edema reduction and healing of wounds in edematous limbs. The spacer fabric would be much more breathable, less insulating, decreasing risk of dermatitis and/or less risk fungal infections than neoprene or Breathoprene type products. The spacer fabric may be woven with different monofilament densities of sizes even within the garment, in order to provide softer padding to some areas and harder padding to other areas. Since some spacer fabrics are woven on a circular knit machine, the machine may be programmed to create padded liners directly with an automated or semiautomated process, either with or without channeling. Such a product has significant cost advantages, and would likely weigh less and lower profile than using traditional foam.

FIGS. 7, 8, 9, and 10 show an exemplary spacer fabric 502 usable as a part of the garment disclosed herein. The spacer fabric may be the sole layer in the garment having sufficient therapeutic compression, or may be laminated to other materials such as woven and or knitted fabrics. FIG. 6 shows a cross section of the garment. The outer layer may consist of a knitted techsheen that is unbroken loop (UBL) compatible. This UBL would be receptive to hook material to provide an attachment mechanism. In this embodiment, the spacer fabric would serve as the inner or middle layer and the UBL the outer layer. The fabrics would be laminated together using a breathable polyurethane lamination technology. This lamination can be done in a matrix configuration to give the greatest breathability to the fabric. In other embodiments, the compression material would comprise of an outer knitted UBL fabric and one to two layers of knitted compression fabric. These layers would each be laminated to provide correct compression. In the preferred embodiment, the materials and stretch chosen would duplicate the compression and stretch characteristics with abrupt end-of-stretch of the Farrow-Wrap™ Classic material as commercialized in 2004. Such knitted techsheen and microfiber compression fabrics and compression UBL fabrics are available from many manufacturers, including Darlington Fabrics of Waverly, R.I. In other embodiments, one of the compression fabric layers would be replaced with a woven fabric. Woven fabrics have rigid end-stretch. A properly chosen compression UBL material from Darlington fabrics and a woven fabric to limit end-stretch could provide very similar performance characteristics of the FarrowWrap Classic™ material. In other embodiments, the compression material is made of compression stocking material, as is known in the art. In this embodiment, standard compression stocking material sewn on a very large circular knit machine or flat-knit compression material (as sold by Jobst Elvarex, Juzo Helastic, etc) can be used. This flat-knit compression material is typically purchased on rolls, so it is suitable to make this type of compression material. Any other compression material or nonelastic material may be chosen for these trim-to-fit embodiments. Ideally the compression material would have very little fraying or running once cut.

Alternatively, the spacer fabric may serve as the outer layer, having its own hook compatible outer layer such that hook material would selectively attach to it. In this case, there would be no need for UBL material as the outer fabric layer of the spacer fabric itself would provide the UBL compatible surface. In other embodiments, the spacer fabric would be the inner layer and have a compression material laminated to the outer surface. The spacer fabric may have channels as illustrated in FIG. 7. These channels would consist of areas of high compression and areas of low compression. The high compression areas would be 0.5-5 cm wide. The low compression areas would be recessed and would be 0.5-5 cm wide. The low compression areas may recessed 1 mm-2 cm from the highest portion of the high compression areas. In the ideal embodiment, the spacer fabric would be 0.5 cm thick with high compression channels 1 cm wide and low compression channels 0.5 cm wide. The high compression areas would be 0.4 cm taller, thus providing a very low profile garment which still effectively channels lymph return.

In this embodiment, the padding layer(s) includes linear grooves 71 which are cut or made during manufacturing. These padded and grooved areas provide low and high areas of compression. Such a spacer fabric has never been disclosed. The spacer fabric material has inherent qualities or higher breathability, lower weight, and increased comfort. By varying the length and size of the filaments extending between the two layers, different densities can be created. The grooves 71 and the padded areas 70 may vary in width and height depending on the application. In some applications, a second layer of spacer fabric material or padding 503 also may be included.

FIG. 8 shows another embodiment of the garment padding layer as a spacer fabric material. This time, instead of channels, the foam is made with taller areas of compression 63 which are square or pyramid shaped with or without tapered sides. In use as a part of a liner with a compression garment, the taller areas are placed in contact with the patient's skin. Then under compression from the compression garment, the taller areas 63 move around under the garment against the skin and the movement is thought to facilitate the breaking up of fibrotic areas of tissue and help soften the tissue over time. FIG. 10 shows another embodiment cross-section with sloped sides to the raised squares 64. It is understood that other embodiments and shaped areas are possible.

In some embodiments where the padding material chosen is foam, the density chosen may reflect the application. It may be closed cell so it does not retain moisture easily, or open cell foam for wound care application or better breathability or other reasons. The foam may be reticulated for better breathability. If foam is used, it may be laminated on one side so that foam is not exposed. The foam may be on the inside or outside of the liner. The foam may serve as the inner layer of the garment, so that the foam layer will provide good friction against the skin to prevent garment slippage. In other embodiments, silicon beads or polyurethane foams or bands will be used on the inner layer of the garment to prevent slippage of the garment on the skin.

In some embodiments, the padding layer may contain multiple holes in it to improve breathability. These holes may also affect the skin surface pressures under the device. The size and location of such holes may be changed to improve breathability, skin surface pressures, and comfort with joint range of motion, depending on the application. For instance, in one embodiment it may be desirable to use padding layer with high hole density or large holes over the anterior ankle area for better breathability, but still use thicker foam or spacer fabric material to better protect the tibialis tendon. It is understandable to one known in the art that other areas of high flexion such as the elbow and knee may desire more strategic hole placement or size to provide optimal padding, breathability, and stretchability to the affected area of the limb. The padding layer in some embodiments would have multiple small holes poked in it to allow for breathing or with dye cut patterns congruent at edges, yet to allow motion at joints and/or to allow for breathing of the liner.

The garment may be single use, a limited re-usable, or re-usable product with long life span. In some embodiments the garment would incorporate antimicrobial materials/chemicals/products into liner material to reduce pathogen colonization and reduce risk of infection.

Figure 18:
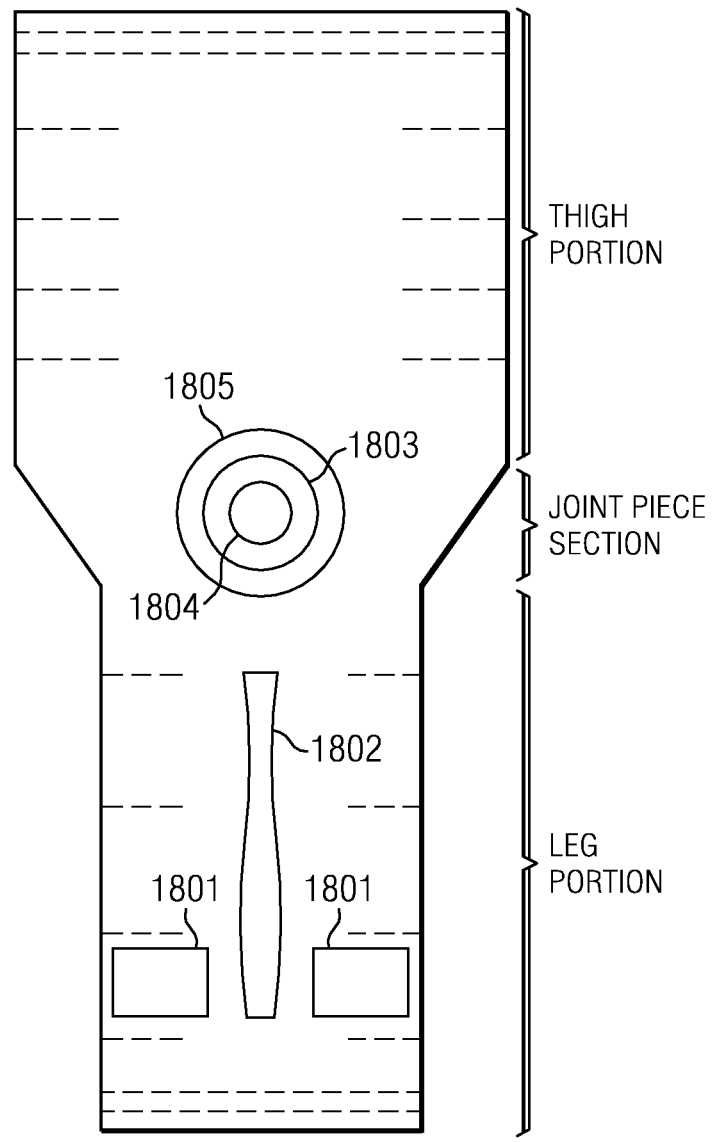
FIG. 18 is an illustration of a compression garment showing areas with additional padded areas.

In some embodiments, some areas of the garment would incorporate additional areas of padding to protect bony areas, and in other embodiments the inner layer may contain padding with channeling to help direct lymph flow and facilitate edema reduction. FIG. 18 shows a lower leg garment with additional padding applied. This padding may come standard, or may be an option when the garment is ordered and is placed at time of manufacture. The padding would be low profile foam or spacer fabric and may or may not have waffling or channeling. The padding may be beveled at the sides for increased comfort. Alternatively, the padding may attach permanently, semi-permanently, or selectively with fabric glue, fabric adhesive, iron-on transfer, or hook and loop technology. This would allow the padding to be removed when not needed, or to be replaced quickly and efficiently if it looses its resiliency. The patient could choose for instance waffled padding to better massage and break up fibrotic areas, or channeled foam to help reduce edema more effectively.

Figure 19:
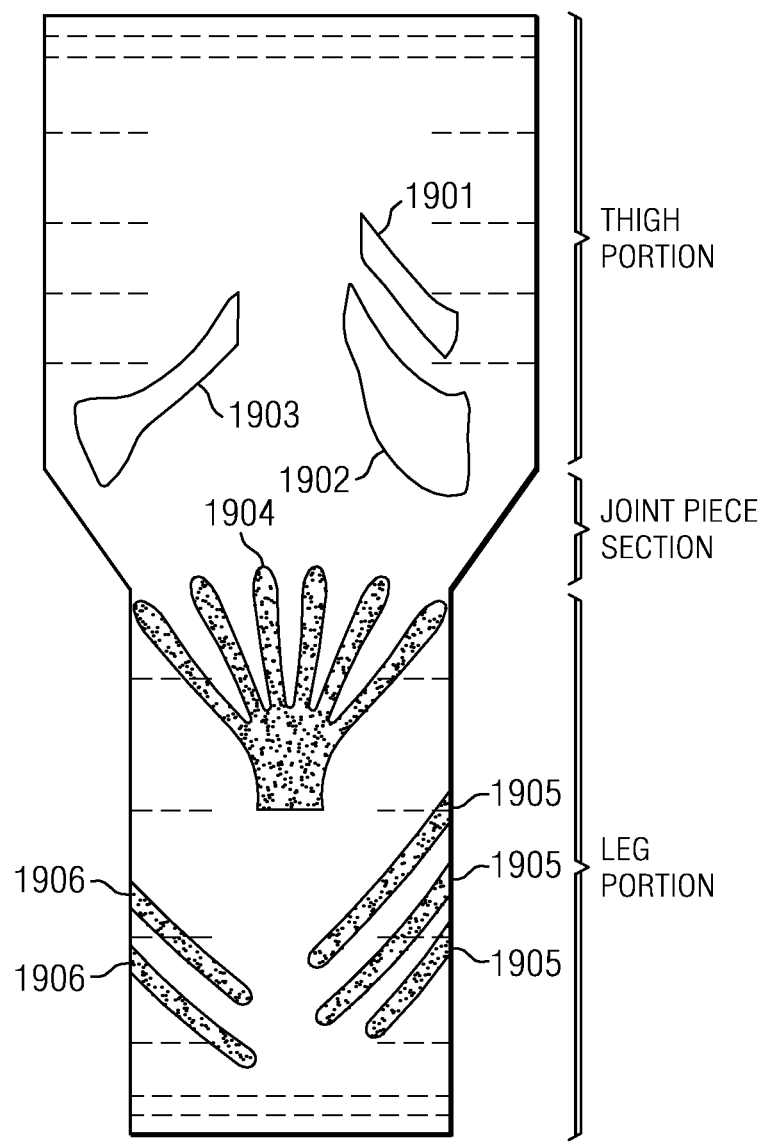
FIG. 19 is an illustration of a compression garment with added features.

Another aspect of the current invention is to include functionality similar to Kinesiotape built into the garment. Kinesiotape is used on the skin to help channel lymph fluid back toward the body along the skin. It functions by providing a semi-rigid attachment to the skin, causing augmentation of the lymphangion micropumps in the dermal layer of the skin. As shown in FIG. 19, semi-rigid materials can be added to the low profile planar compression material. These materials are depicted in 1904, 1905, and 1906. In 1904, the semi-rigid material will move against the skin under the compression wrap and augment lymphatic drainage in this area outwardly and upwardly. This is particularly useful to follow natural lymphatic flow patterns in the skin. In the case of 1904, the material is draining an area of regional lymphostasis due to trauma and infection. This increased rigidity material could be applied to the garment at time of assembly or manufacture, time of fitting, or replaced by the patient during garment use. The increased rigidity material may help augment superficial lymphatic flow to reduce edema to the area. The increased rigidity material may or may not contain tacky tape material on the side facing the patient so that it would adhere to the patient's skin. Such an invention may be preferable to products like Kinesiotape because it would be attached to the garment and have longer life, and may also serve to hold the low profile compression garment in place. Once the product loses its tackyness, it could be removed and replaced as needed. Since the limb would be moving against the compression garment, this would effectively result in tenting and compression of the underlying skin in areas where the semi-rigid material with tacky surface was applied. The effect would be to augment the lymphangion micropump much in the way that Kinesiotape works. Alternatively, the materials 1904, 1905, and 1906 may represent a skin-friendly double sided tape or sticky material to help prevent garment slippage. Other geometries are possible and these are shown only as representative examples.

In some embodiments, the compression garment is a garment having short-stretch properties and may be any of the garments disclosed in U.S. patent application Ser. No. 10/975,590 filed Oct. 28, 2004, U.S. patent application Ser. No. 11/733,991 filed Apr. 11, 2007, and U.S. patent application Ser. No. 12/391,051 filed Feb. 23, 2009, all three of which are incorporated herein in their entirety by reference.

Using garments having the properties of short-stretch provides many benefits to a patient. A user can stretch the garment section and see and/or feel when the maximal stretch level is reached because the garment section may have a limited stretch range. Using this, the user can 'dial into' the correct level of compression when applying the garment, without needing to use a pressure sensor or an indices-type system to determine the correct compression level. This provides a very simple, but very reliable, method of reproducing the correct level of compression every time the garment is donned. Because the garment section is applied at or near maximal stretch, it will not stretch much further. Therefore, the garment provides maximal augmentation of the calf muscle pump and the more the leg tries to swell, the more the garment will work to prevent swelling. Thus, such a short-stretch garment has a high static stiffness index, which has been suggested to measure efficiency of the bandage/garment on the augmentation of the calf muscle pump.

The garment can be designed to be a single use disposable device, or can be designed to be reusable. For severe venous ulcerations with lots of drainage or bioburden, the garment can be designed to be of disposable materials similar to those used in multilayer compression wraps or diaper technology. For mild draining ulcerations, the garment can be designed to be re-usable. In some embodiments, the garment can be used to heal the ulceration, and then the user can continue using the garment for maintenance compression in order to prevent recurrence.

The garment can also be designed to provide graduated compression. For a typical 30-40 mmHg compression stocking, for example, there can be 30-40 mmHg compression at the ankle, but perhaps 20-30 mmHg at the calf level, 15-20 mmHg in the distal thigh, and 8-15 mmHg in the proximal thigh. Graduated compression provides more compression distally on the limb than proximally, and compensates for gravity to provide optimum compression levels. Different embodiments of the garment can include one of the features listed below to provide a garment with graduated compression. The features listed below can also be mixed and matched to provide graduated compression by combining these various modalities in combination to provide a sophisticated garment with various compression levels. The garment may have different indicia on where to cut and trim the size of each appendage. For an embodiment where the garment is supposed to provide 30-40 mmHg range compression, for example, the materials and trim locations may be such that when the user dons the garment according to instructions, it stretches the fabric and generates the 30-40 mmHg range compression on the garment section. Alternatively, the same garment may be marked with indicia to create wider appendages, such that the user stretches the material with the same compression it is applied to a wider limb portion, and thus has less compression in the 20-30 mm range. By changing materials and indicia and trim locations, a wide variety of garments can be manufactured.

Spacer Fabric as a Compression Garment

In some embodiments, the Spacer Fabric may be used to make not only a liner for use with a compression garment, but may be used to make a compression garment itself The spacing and filaments between the layers provides cushioning or air padding. Thus, in this embodiment, the garment itself is a padded compression garment. In one embodiment, the Spacer Fabric would be generated to create a short-stretch range of compression 15-90% maximum stretch with resting compression at end stretch of 15-20 mmHg, preferably with fairly abrupt end-stretch so that the user can feel when the band no longer stretches. The outer surface of the Spacer Fabric can be generated to have Velcro®-type hook compatibility, and the opposing bands can be secured in place with standard hook material. This garment would ideally have relatively abrupt end-stretch or bandage lock-out so that the user can readily identify when the garment is applied at maximum stretch. This embodiment may be excellent for postop surgical use and hospital use to prevent DVTs in patients, for example. Examples of compression garments that may be formed spacer fabric were disclosed in U.S. patent application Ser. No. 12/391,051 filed Feb. 23, 2009. Other embodiments may have 8-50 mm compression when applied at end-stretch to a limb portion.

In another embodiment, the spacer fabric would be laminated to a woven and/or knitted stretch or compression fabric (s) or UBL (unbroken loop fabric) to provide therapeutic compression levels. In one embodiment, the garment would consist of Spacer Fabric with UBL on the outside of the garment. This garment would utilize polyurethane or other lamination technology as is known in the art. In another embodiment, there is a woven fabric which provides the end-stretch on the inner layer, a spacer fabric to provide padding, and an outer layer of UBL material which also provides the majority of the compression. Other embodiments are possible, depending on materials and properties chosen. The compression fabric could be knitted of Rochelle or Tricot or another knitted weave, or could be a woven fabric. The laminated fabric could provide the compression, the bandage lockout or a combination of both, such that the combined layers provided therapeutic resting compression level of 8-50 mmHg at or near end-stretch when applied to a limb at rest, and a maximum elasticity of 15-90% maximum stretch with preferred maximum stretch which lies within the range of 25-50% maximal stretch. Additionally, the laminated woven or knitted fabric could provide the Velcro®-like hook compatible surface, as is known in the art. The fabric(s) could be located on the inside or the outside of the spacer fabric or both. The combined result would be correct compression level and built in padding to prevent injury to the limb. Woven fabrics are especially valuable in designing such a system due to their ability to be designed with abrupt end-stretch.

In some embodiments, the garment is formed to have properties of a short-stretch material to apply compression to the limb. In the embodiments including padding, the padded compression garment distributes compression loading about the bony areas in a manner that makes wearing the compression garment and liner relatively comfortable for the patient.

Although disclosed as being used over the foot and leg, it is also contemplated that the garment disclosed herein may also be used to treat the arm, shoulder, hand, wrist, knee or other portion of a limb on a patient or an animal. In some embodiments, the padding is spacer fabric while in other embodiments, the padding is chipped and/or channeled foam mixed with smooth foam over the aforementioned areas.

Trim-To-Fit Compression Garment

Correct fitting of compression garments to limb shapes necessitates custom and off-the-shelf varieties. Foot length varies considerably, and there is variation in width and therefore circumference of feet, as well as considerably variability in ankle and calf circumferences and shapes, as well as height. The same applies for thigh high and arm and hand sizes. Most compression garment manufacturers, therefore, use custom and off-the-shelf solutions to fit a wide range of patient sizes. The custom garments, however, take time to manufacture. It is not uncommon, for instance, for custom compression stockings to take one month or longer from date of order until the patient receives the garment. Furthermore, errors in manufacturing and measurement sometimes necessitate remanufacturing the garment or altering the garment in order to get a proper fit. This is very inconvenient for the patient, who needs therapeutic compression immediately, and must make-do with an off-the-shelf garment or bandage until the custom garment arrives and fits correctly.

Furthermore, in some patients, compression is needed over the distal forefoot, at the level of the metatarsal heads, in order to prevent lymphostatic pooling of edema in this area. In other cases, it is desirable to avoid compression over the metatarsals in order to reduce chance of injury due to pressure directly over a bony surface. The ability to make these clinical decisions and take immediate steps to provide a correctly sized and suitable garment is very important in order to provide proper therapeutic compression safely and effectively in a patient.

Lastly, patient limbs vary in geometry from conular to tubular to other odd-shaped morphologies. At present, when a band is wrapped horizontally about a limb that is conular, it is tighter around the wider, more proximal portion while being looser around the distal, more narrow portion. The net effect of this is to promote the likelihood of the band sliding down the limb, which becomes more problematic on more conular-shaped limbs.

What is needed, therefore, is a garment system that is customizable at point of sale to patients by a medical equipment company, clinic, hospital on site, or even by the patient themselves so that the garment is immediately available and correct fit can be established with on-site customization that is simple, reliable, and predictable. One way of customizing as described uses a trim-to-fit solution permitting providers and even patients to trim the garments to provide a proper size while also providing proper and desired compression levels.

For the trim-to fit solutions, the material would ideally be short-stretch material or a material having properties of short stretch, with maximum elasticity of 15-90% such that the garment provides a compression level that falls within the range of 8-50 mmHg, when applied on a resting supine limb at or near end-stretch. It is understood however, that non-elastic or moderate-stretch or long-stretch embodiments may be chosen. A variety of standard materials known in the art for treating swollen limbs may be used for this invention. It is understood that the appropriate choice and location of markings would take into account the stretch of the material in order to properly trim and fit the garment to the patient.

The desired materials and configurations should not fray significantly when cut, and also should not run easily where cut. It is important that the compression materials be as breathable as possible to prevent dermatitis and increased fungal colonization of the skin. Some embodiments of the garment will include 2-3 layers of knitted compression material. The outer material in the preferred embodiment will consist of a UBL material. The garment may have a thin spacer fabric on the inner or middle layers. Woven materials may be combined with high quality knitted compression materials to provide abrupt end-stretch. The woven materials have very abrupt end-stretch, which allows the user to feel when they are at the end of the stretch of the material. When the user no longer feels the material stretching, they can thus reliably and predictably apply a known compression level to the limb. The materials and construction are then chosen to get the correct performance.

For one preferred embodiment, a 1 way stretch material may be preferred in order to maximizing working compression and minimize band narrowing as it is pulled. In order for the garment to fit best, however, it may be desirable for the material to stretch at least 5-25% in the direction parallel to the axis of the limb.

By determining limb size and where to trim each band, the garment can fit a wider range of patients. In addition, it can be used for active treatment phase edema reduction as the garment size may be reduced as the edema reduces. This is achieved by the patient trimming back the appendages as needed as the limb girth reduces. By allowing the patient to trim the garment back as edema reduces, the garment maintains maximum therapeutic function and minimizes excess material overlapping, which may make the garment more insulative, more difficult to apply, and in some instances impossible to apply. Additionally, it is important that the patient properly trim and don the garment to achieve the desired compression level. This requires the patient to overlap the material a specific amount. Thus, the patient may be treated and released in the same garment creating great cost savings for both the patient and health system. This allows the garment to be trimmed to shorten it in an easy and reliable manner in order to better fit the patient. After acute phase edema reduction, the patient is at their baseline and no further edema reduction is possible. The patient can then continue to wear their compression garment, resulting in additional cost savings.

By creating each garment with the upper band(s) as separately attachable and/or trimmable, there is no reason to stock short, regular, or tall garments, reducing inventory and increasing the likelihood that the trim-to-fit garment can fit any given patient population. This is especially important for Durable Medical Equipment companies, hospitals, and clinics, who would prefer to stock fewer sizes to fit their range of patients. By reducing inventory, cost savings are realized. By having customizable features, the garment can better fit any given patient.

Figure 3A:
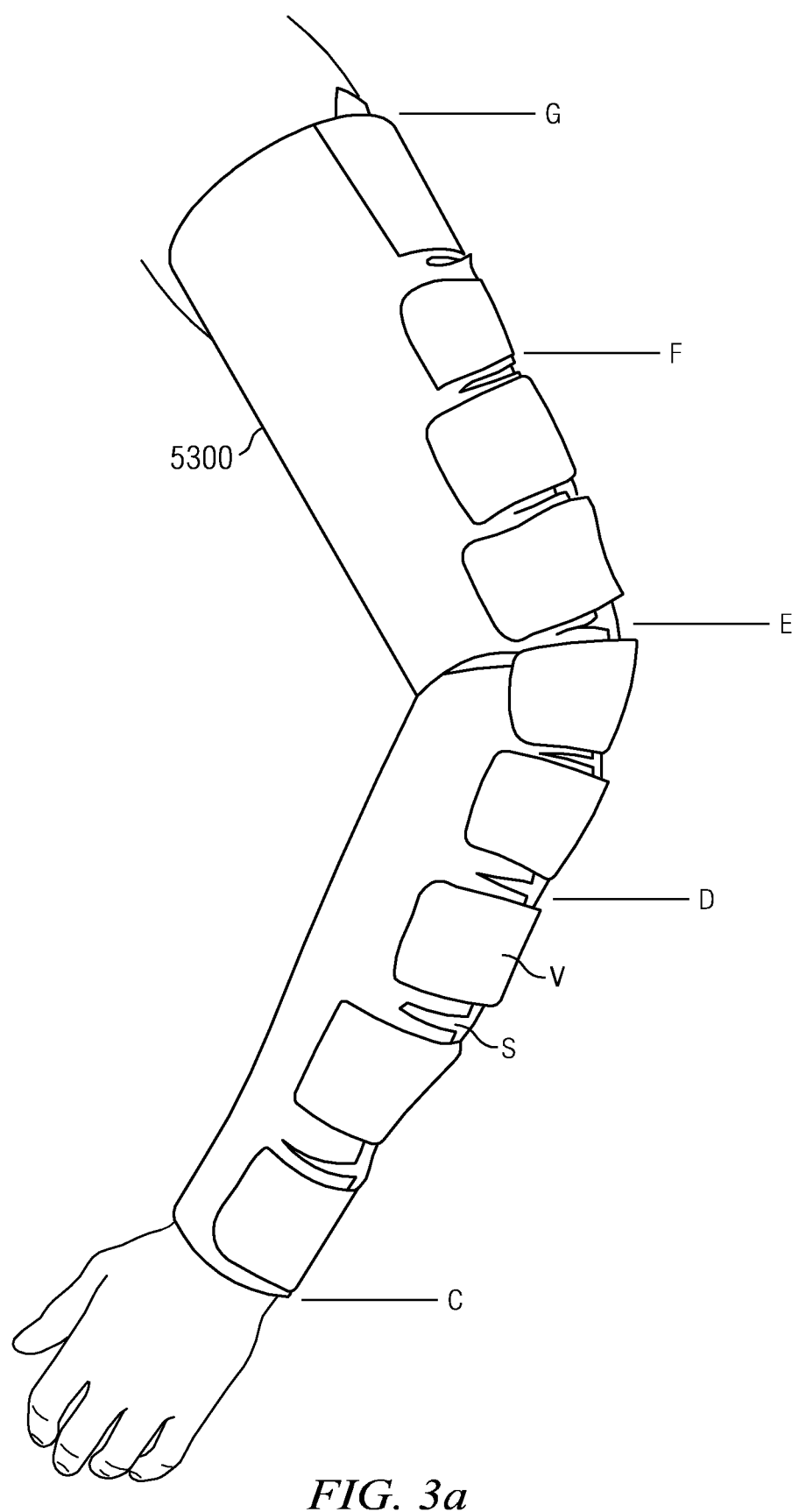
FIG. 3a is an illustration of a compression garment applied to an arm.
Figure 3B:
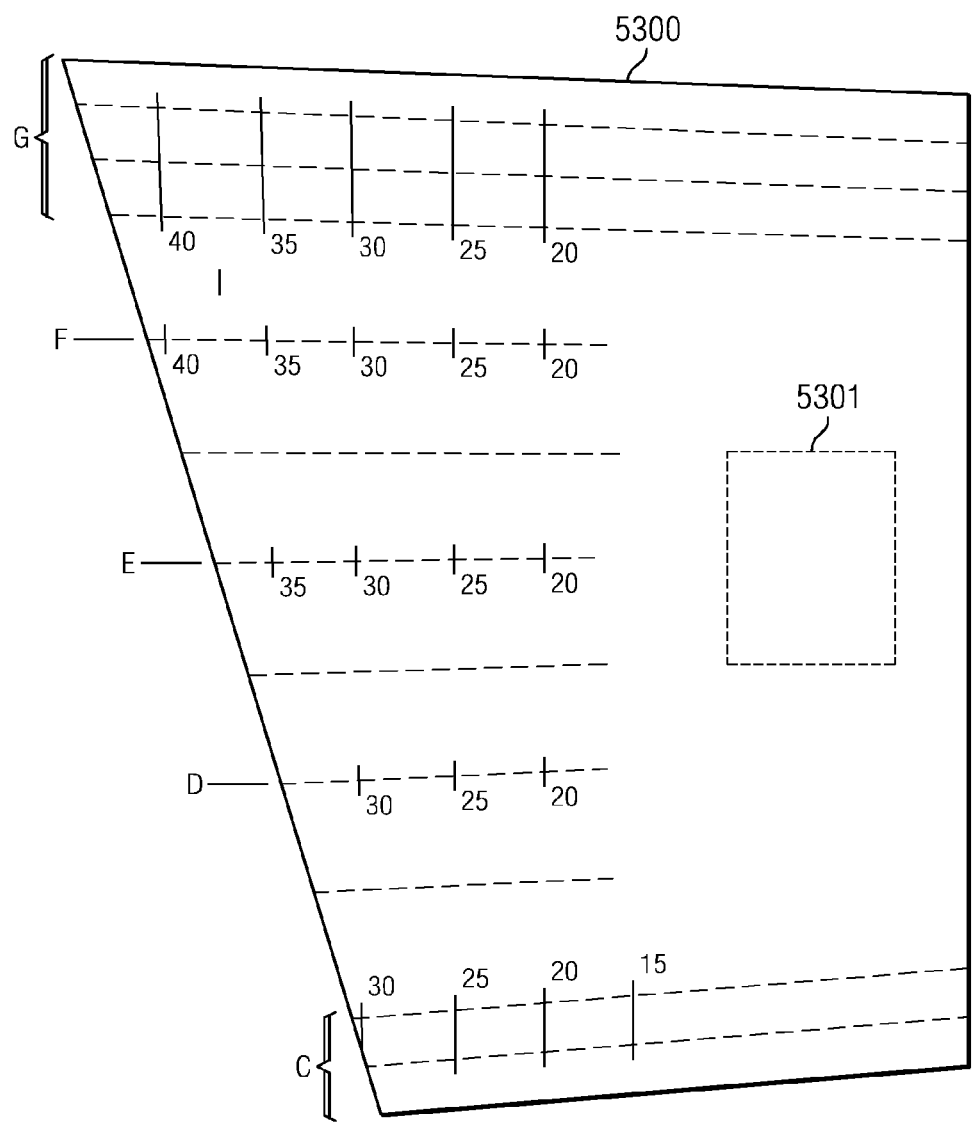
FIG. 3b is an illustration of the garment of 3a prior to trimming and fitting.
Figure 3C:
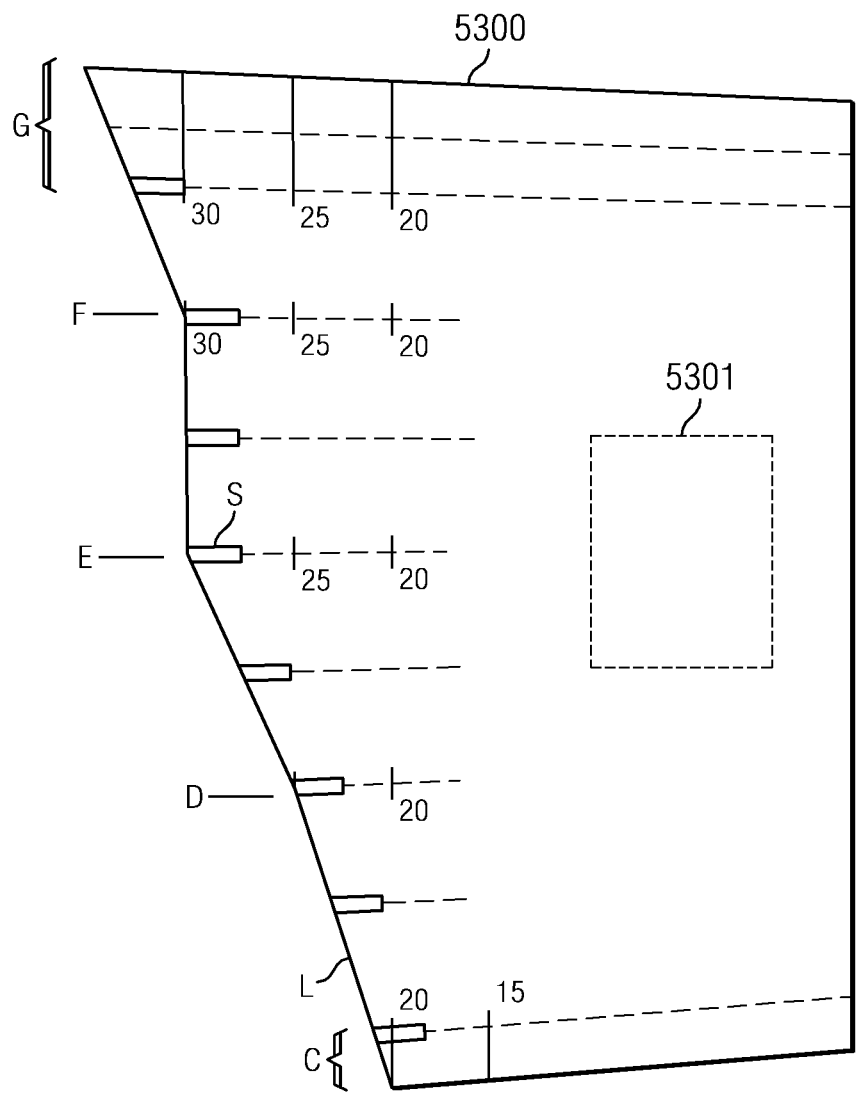
FIG. 3c is an illustration of the garment of 3b after trimming to fit the patient's limb.

FIG. 3 a, b, and c show one embodiment of an off-the-shelf customizable armpiece of the present invention using a trim-to-fit design. FIG. 3b shows exemplary details of the armpiece as provided in an off-the-shelf configuration, FIG. 3c shows the same armpiece in its customized form which has been trimmed to fit a specific patient's arm. and FIG. 3a shows the arm garment applied to a patient's limb.

In this embodiment the armpiece is similar to an off-the-shelf garment, but different in that fewer sizes are required and it is immediately customizable at the point-of-sale such that the patient would be provided with a custom garment having a proper fit and proper compression levels and compression gradients at the time of the patient's visit. The armpiece may be made from a single piece of material without the need for individual bands. It may have markings thereon which indicate locations for trimming the armpiece to obtain a proper fit to the patient's arm dimensions, which would also result in proper and safe compression levels and gradients when the garment is applied. The armpiece is designed in a way that allows the patient to apply the garment to the limb while using only one hand. Conventionally, a patient with one affected arm is often dependent on others for applying a compression garment or bandage to the affected arm, which may be inconvenient or, at times, may be harmful to the patient if assistance cannot be found. Traditionally, trained practitioners may also be needed for application and readjustment to insure that safe compression levels and compression gradients are administered and maintained.

The armpiece features indicia that have been printed on or otherwise applied as a guide for trimming according to actual measurements of the patient's arm. The indicia may display actual length measurements or a compressed scale using the formula disclosed herein. Regarding the patient's arm length, this could use a compressed scale but generally the trim lines at the top and bottom of the garment will be in a 1:1 ratio with the actual arm length.

However, the indicia that mark trimming distances for arm circumferences along the length of the patient's arm may not be in a 1:1 ratio with the actual measured arm circumferences. Instead, an algorithm can be used for determining a variance between the actual circumferences measured on a patient's arm at predetermined locations along the patient's arm and the actual distances on the armpiece corresponding to each measured circumference. The circumference trimming indicia that are printed on the armpiece correspond to the pre-calculated values according to the algorithm so that the armpiece, when trimmed and applied, would provide proper compression at each circumference along the arm length for safe compression gradients, would allow for an overlap percentage gradient which is greatest at the smallest circumference and smallest at the largest circumference, and would prevent windowing.

The actual measured arm circumference would correspond to a likewise numbered indicia on the armpiece. However, the value indicated by the armpiece circumference indicia and the actual distance along the armpiece circumference may not be equal. For example, if the measured circumference at the wrist crease of a patient is 15 cm, then it would correspond to a location on the armpiece at a likewise numbered indicia of 15 cm. However, the 15 cm indicia on the armpiece may have an actual distance of 18 cm along the armpiece circumference which would allow for 3 cm of overlap. At the 15 cm indicia, a 2.5 cm slit may be cut which would form the band. The 3 cm of overlap having a 2.5 cm slit would sufficiently cover the wrist crease and would prevent any windowing. Similarly, the other areas of the armpiece where slits are cut would result in proper overlap and no windowing. Thus instead of a percentage overlap, a fixed amount of overlap may be built into the indicia system.

The patient's arm length is obtained with two measurements. One is from the wrist crease to the elbow crease CE, and the second is from the elbow crease to the axilla EG. The armpiece is trimmed for length at the distal end to correspond to the measurement CE, and at the proximal end to correspond to the measurement EG. The overall length of the patient's arm, thus, the overall length of the armpiece is the sum of CE and EG. The purpose for this dual measurement is for consideration of varying upper-arm to forearm ratios among different people, and realization that the proper fitting and trimming will start with the elbow and work proximally and distally outward. This is done so that there are not attachment mechanisms overlapping the antecuboidal fossa of the patient's elbow region.

The arm circumferences are measured at C the wrist crease, D the wide forearm, E the elbow crease, F the bicep, and G the axilla. These measurements are transferred to the appropriate lines marked C through G respectively, on the armpiece. Having transferred the measurements, lines may be drawn in a connect-the-dots fashion distally to proximally from C through G to establish a trim path. Alternatively, the lines may be drawn in stair-step type configuration perpendicular to the cuts made to create the appendage. The armpiece now may be trimmed along the trim path. At each intersection of the trim path with a horizontal band line, a 3.5 cm slit is cut into the garment to form a total of nine appendages, in this example. (See FIG. 3c) These appendages serve as miniature bands and allow the user to pull the attachment mechanism around circularly over the garment and the user can adjust the vector force more proximally or distally as needed for comfort and better fit. It is to be understood that geometries other than linear slits may be used for forming the appendages, and the depth and width of the appendages may vary depending on the chosen embodiment. Other shapes are possible as well. For example, the appendages may be formed with Y shaped slits, V shaped slits, ovals, rectangles, trapezoids and any other shapes. Further, it is understood that other cuts may be used for increased flexibility and reduced pinching at the elbow joint. These other cuts may be of any geometry that would facilitate comfort and flexibility while maintaining therapeutic levels of compression. For instance, in other embodiments, the garment may be trimmed at right angles to the appendage-like slits, creating a stair-step type configuration.

For this exemplary embodiment, the attachment mechanism preferably uses hook and loop material although other attachment means are anticipated. The eight most distal bands may be attached using similar sized hook and loop fasteners with the most distal band having a fastener which may be trimmed to accommodate arm length. The most proximal band may use a larger sized hook and loop attachment which may be, again, trimmable for arm length.

In order to achieve a desired compression (in this embodiment 20% is chosen but other ranges are possible) of approximately 20% maximal stretch with a safe distal to proximal compression gradient, the circumference indicia at each band line is shortened to 4.5 cm for every 5 centimeters of actual measured arm circumference. In other words, the circumference indicia are exaggerated by 3 cm to accommodate overlap without windowing, as explained above, but then are reduced to 4.5 cm for every 5 cm thereafter.

The patient may don the armpiece by first attaching it at the wrist which has maximal percentage overlap and then work their way up the arm attaching each appendage in turn where each subsequent appendage has a lower percentage overlap, and finally, at the axilla where there is a minimal percentage of overlap but which has a larger hook and loop material for attachment.

In other embodiments, there may be no appendages. Instead, the attachment mechanism may simple attach to the edge of the garment at the indicated location. Sometimes the attachment mechanism will be sewn or RF or ultrasonically welded in place. In other cases, fabric glue to adhesive will be chosen. In other embodiments, hook and loop material may be chosen. Furthermore, the attachment mechanism may consist of short-stretch, moderate-stretch, non-elastic, or highly elastic bands or webbing. The attachment mechanism may consist of b-rings, buttons and hooks, or any of a number of other methods as are known in the art.

Figure 11:
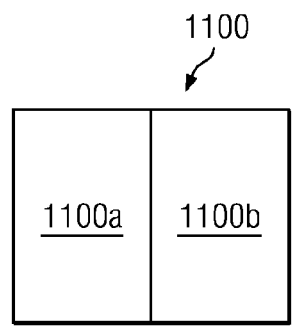
FIG. 11 is an illustration of an attachment mechanism.

Attachment mechanism 1100 of FIG. 11 is used to connect the ends of appendage 1301. The attachment mechanism 1100 may start on the outside of the overlapping band on either side. This is advantageous, as the trim-to-fit legpiece can therefore be made such that the attachment attaches to the inside or to the outside (medial or lateral side) of the legpiece, depending on patient ability and preference. In most embodiments, the patient will want a Velcro®-like attachment mechanism that is utilized such that it is on the outside of the legpiece so the Velcro®-like attachment mechanism does not rub against each other medially on the limb.

The attachment mechanism 1100 may have sections 1100a and 1100b. One of the sections may be permanent or detachable but with greater holding strength than the opposite end. For example, if section 1100a of the attachment mechanism used standard Velcro®-like attachments, and section 1100b used more industrial strength Velcro®-like attachments, then section 1100b would be designed to be applied to the end of the band. The user would then overlap the bands appropriately and use section 1100a during daily use to don and doff the garment, leaving section 1100b attached. Section 1100b could be removed, however, for instances like washing the garment in a washing machine, where the Velcro®-like hook and loop could increase wear or cause garment entanglement which would make garment less easy to clean and use on daily basis.

One example of a preferred embodiment of the attachment mechanism uses HiTex corporation HTH-833 as section 1100b, and HitTex corporation trihook-150 BEI as section 1100a. Because HTH-833 is very aggressive hook material and very difficult to remove, it would be designed to stay attached to the end of appendage 1301 long term. The patient would then remove and apply section 1100a during daily use. The entire attachment mechanism 1100 could be removed during weekly washing and on an as needed basis, and the rest of the time the patient would wash the liner daily with the compression garment.

In this embodiment, the attachment mechanism is already in place on the garment 1300 and the garment is provided as an off-the-shelf (standard) sizing or has already been trimmed custom for the patient. In one embodiment, the attachment mechanisms 1100 represent pieces of Velcro®-like materials that are permanently or semi-permanently attached using a method that is known in the art such as sewing, RF welding, gluing, or ultrasonically welding into place. The attachment mechanism is divided between the markings on the garment, in order to facilitate easier trimming of the garment to properly fit the underlying limb portion.

Figure 12:
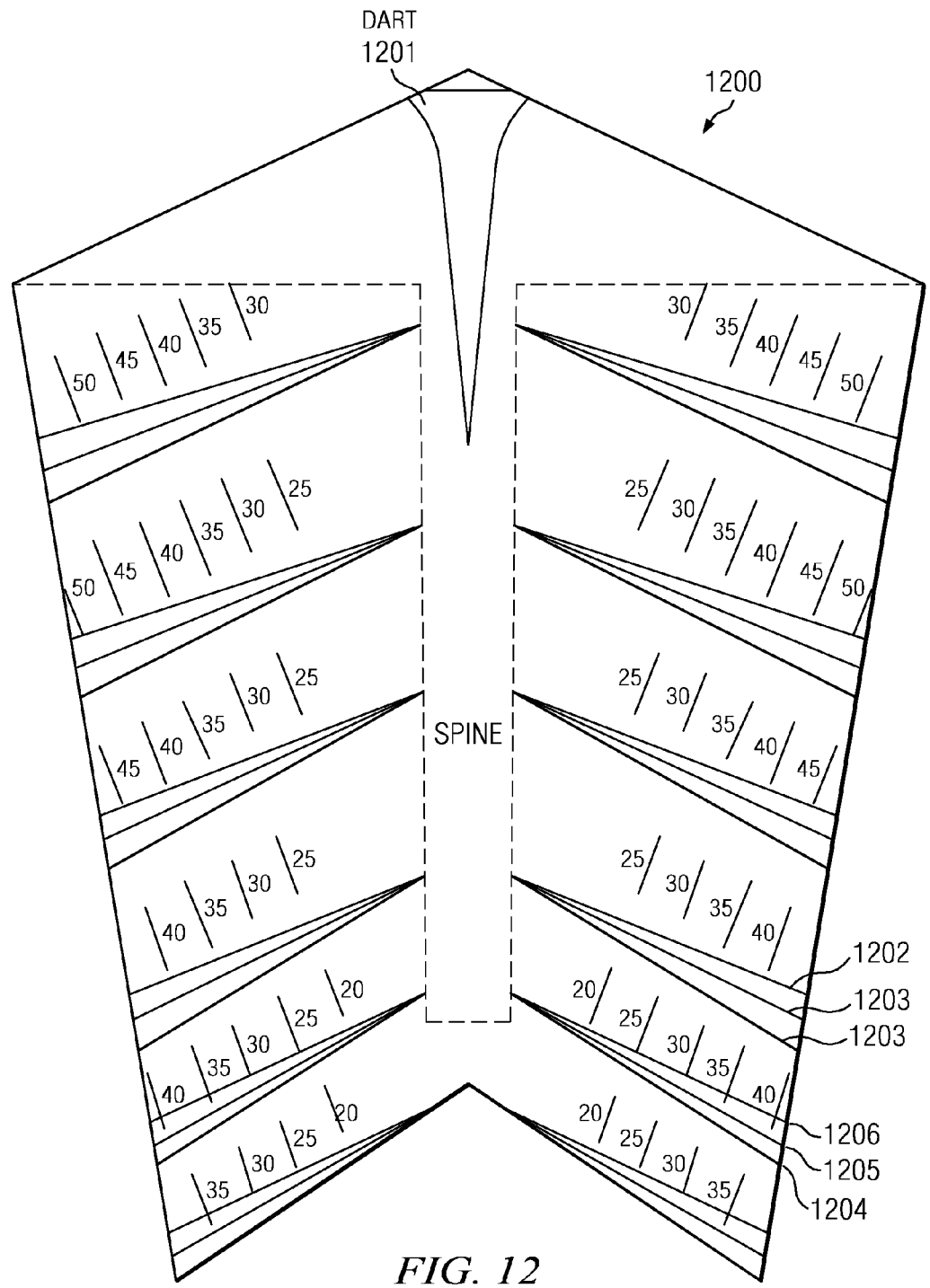
FIG. 12 is an illustration of a single sheet of compression material for a legpiece.
Figure 13:
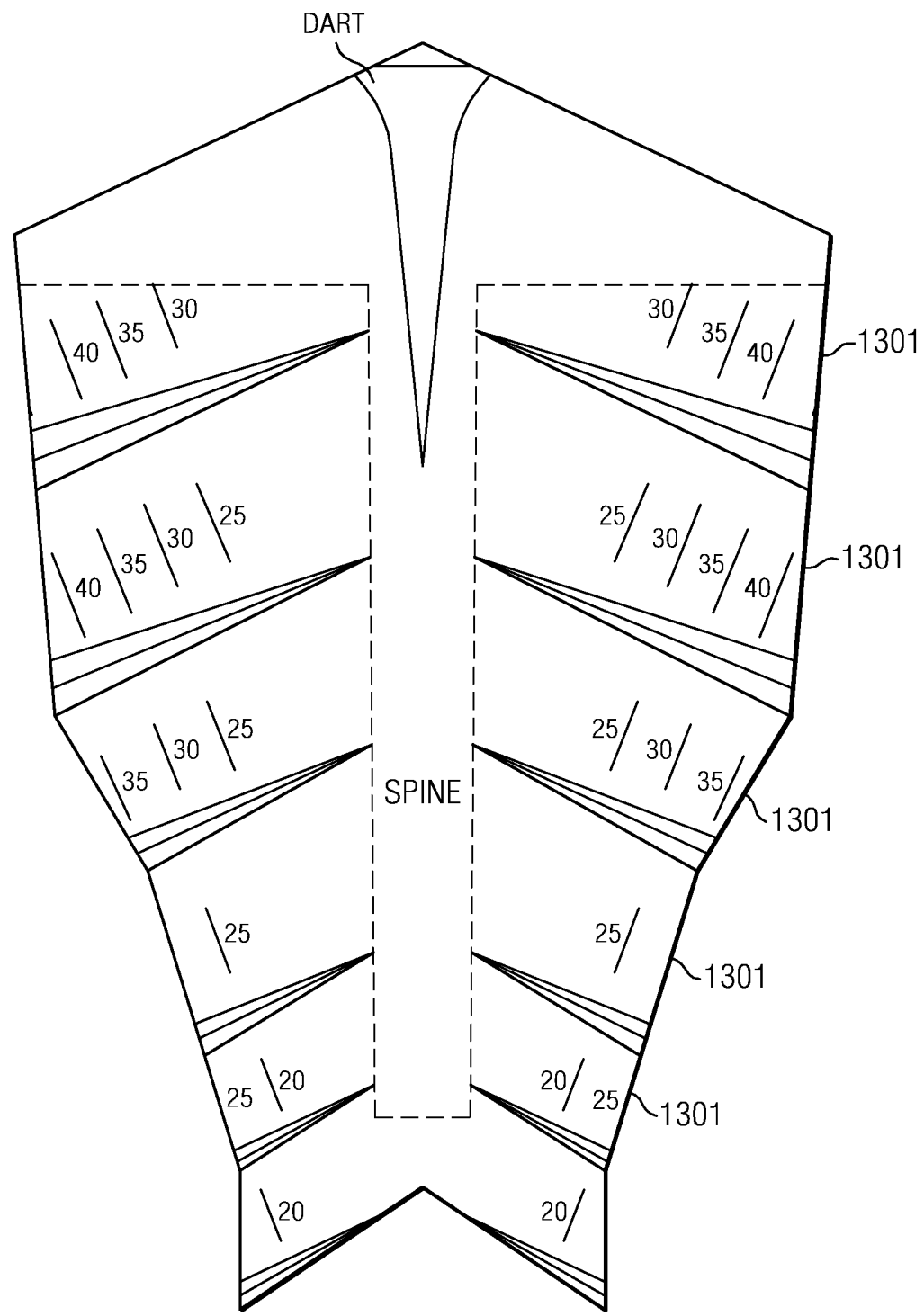
FIG. 13 is an illustration of a single sheet of compression material for a legpiece after trimming.
Figure 14:
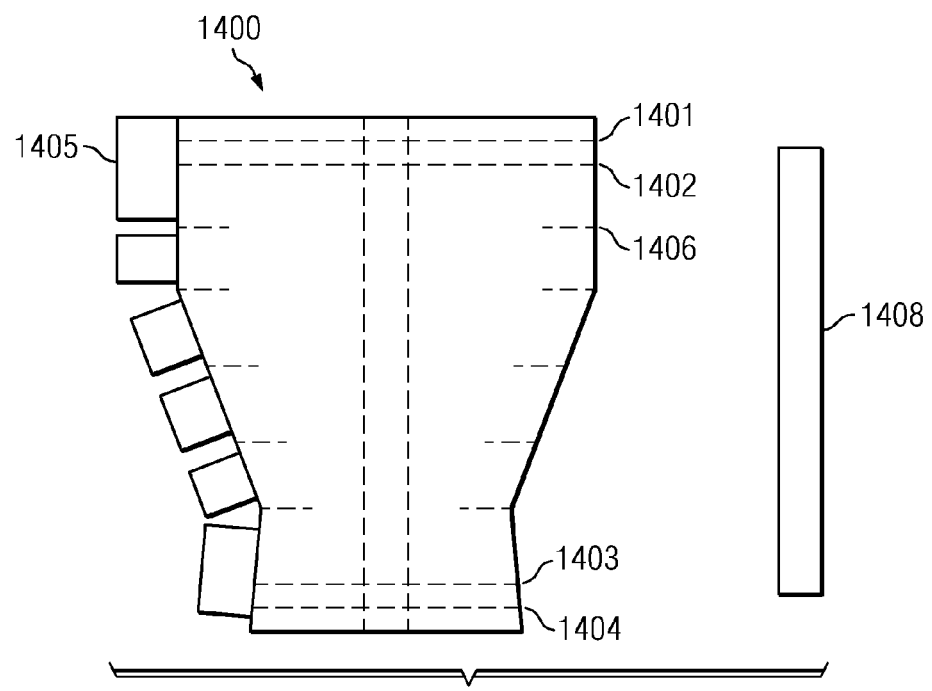
FIG. 14 is an illustration of another embodiment of a single sheet of compression material for a legpiece.

FIGS. 12 and 13

In another embodiment, attachment mechanism 1100 may be one large piece with the markings on the attachment. Here, the garment can be safely cut to size as desired along the lines to create appendages even though the attachment mechanism is already attached, and still work properly and reliably. For instance, the garment may be provided with attachment mechanisms in place, and the patient may trim only the lower portions of the garment 1403 and 1404, or the upper portions of the garment 1401 and 1402 in order to get the proper length. A measurement form and instructions would assist the patient in the correct trimming of the garment height. In some embodiments where the attachment mechanism was already permanently attached, the trimming may include trimming the attachment mechanism 1405. If the attachment mechanism is ultrasonically welded to the garment, for example, it is reasonable that the trim line of the garment could include the attachment mechanism and not affect or weaken the permanent weld of the attachment mechanism to the garment. The cuts, which may be vertical, horizontal, and/or angled, may optionally create appendages 1406. The depth of such cuts could depend on the patient's measurements or be a fixed amount and used a parameter to guide the patient in the correct donning procedure. For example, the patient would pull the base of the slit across the opposite and opposing side a fixed amount, say 1 cm, which would cue the patient into the correct tension to apply during donning as an instrinsic feature of the garment, obfuscating the need for any additional indice system. If the garment is sold as an off-the-shelf sizing with permanent attachment mechanism of hook material, the cuts may already be made. If a selectively detachable attachment mechanism is used, then the patient would use a measurement form and follow the indicia on the garment to instruct them where to trim the garment for proper fit. 1409 shows an optional spine material which can stiffen and reinforce the spine. This spine 1409 may be sewn in place at time of manufacture, may come in the trim-to-fit as an included or optional feature. In this case, the spine may adhere with fabric glue or adhesive or be selectively detachable with hook and loop or use other methods as are known in the art.

Figure 17:
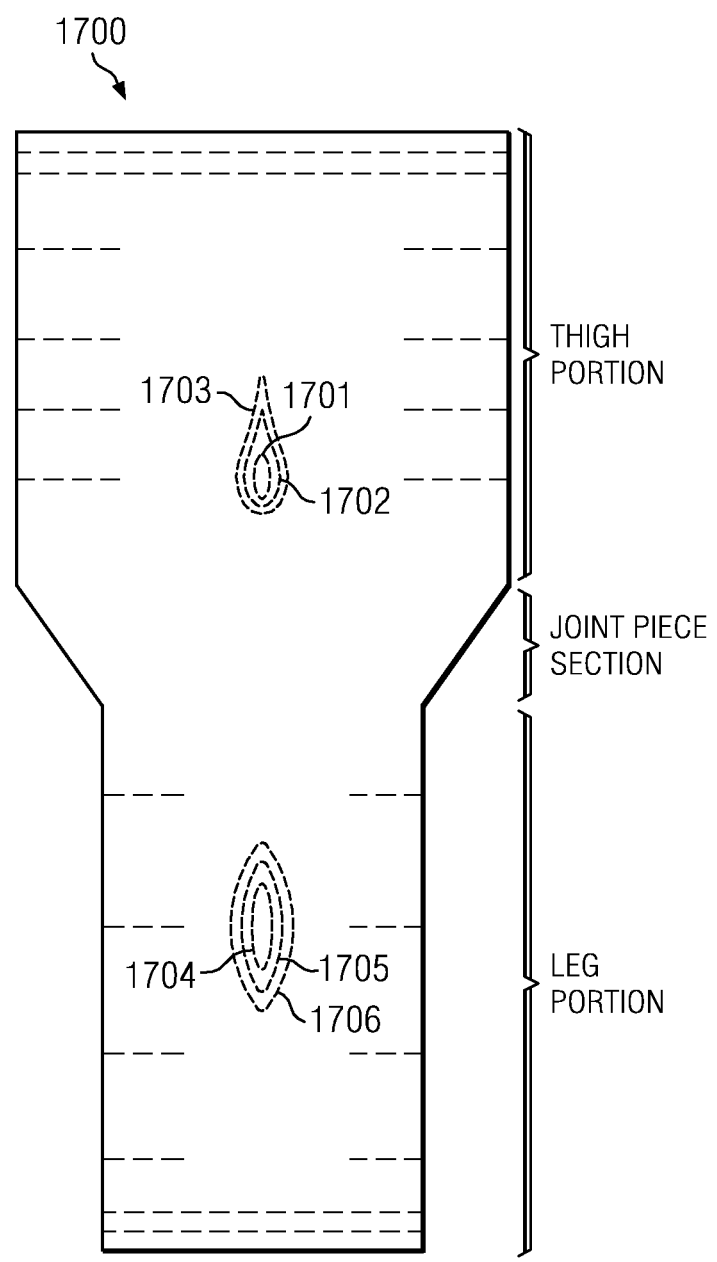
FIG. 17 is an illustration of a compression garment showing areas where additional material can be added to compress and lift a lobule.

FIG. 17 illustrates a legpiece trim-to-fit garment. In this embodiment, there are markings or indicia to remove material from portions of the spine. This is sometimes useful to make the garment better anatomically fit the limb. For instance, around the belly of the gastrocnemius muscle (back of the calf), the limb narrows above and below the muscle belly. By trimming out a small ellipse of material in the spine, the garment may better fit and reduce gathering and bunching. This type of design is most needed when there is a sharp rate of change of diameters from one limb section to another limb section. These sections may be removed at time of manufacture and the opposing sides permanently reattached (with zig-zag stitch, for example), or this may be an option done at time of fitting the garment for the patient. 1704, 1705, and 1706 illustrate different trim to fit locations to remove material in the posterior of the garment just below the calf muscle and induce concave shape into the garment. 1701, 1702, and 1703 show alternative trim locations on the thigh to induce a concave shape to the garment. Note that 1704-1706 are elliptical and 1701-1703 are tear-shaped. This is for illustration to show that other shapes are possible, depending on the limb geometry and the concavity desired. These areas may be trimmed at time of manufacture or could be trimmed as needed at time of fitting or by patients, utilizing hook and loop material or other methods to reapproximate the sides.

Figure 15A:
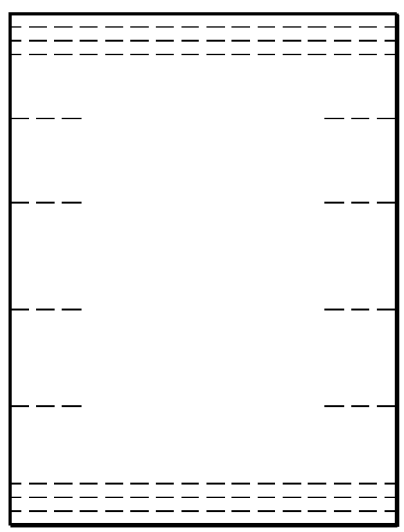
FIG. 15*a* is an illustration of another embodiment of a compression material for a legpiece prior to trimming.
Figure 15B:
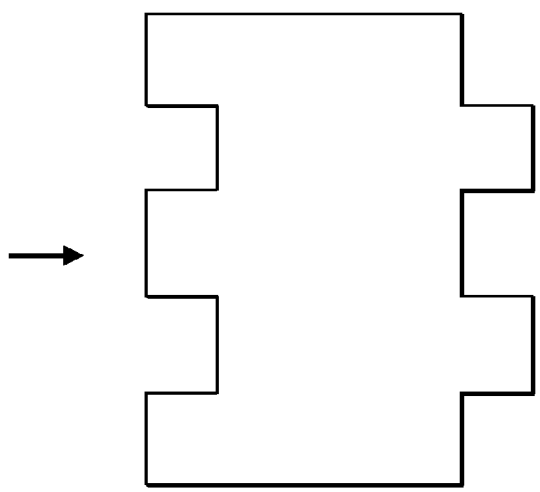
FIG. 15*b* is an illustration of FIG. 15*a* after trimming. In this case, the trimming was done on opposing sides.
Figure 16:
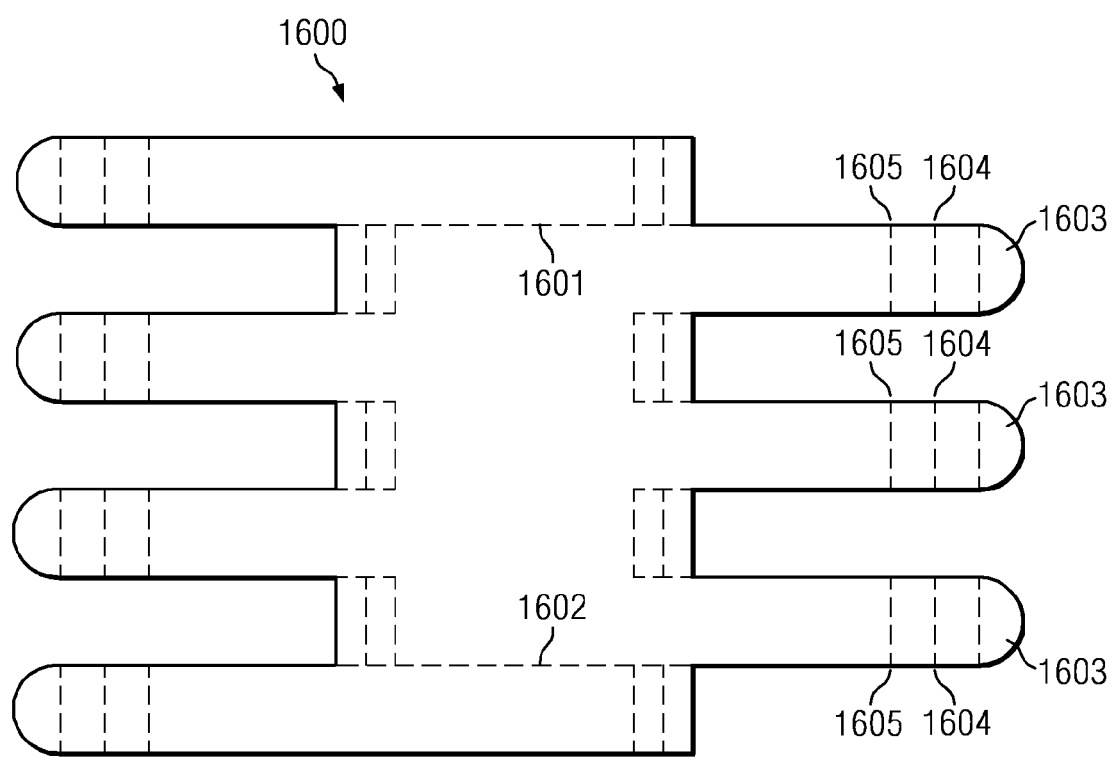
FIG. 16 is an illustration of another embodiment of a compression garment with trim-to-fit indicia and markings.

FIG. 15a illustrates a compression garment with indicia and markings for a legpiece. FIG. 15b illustrates the garment after trimming-to-fit using concept of opposing bands. FIG. 16 shows an alternate embodiment of a trim-to-fit garment with opposing bands. In FIG. 15a, the trimming can be done on both sides of the garment or on alternating sides. This shows the power and ease of flexibility in which the garment can be customized. The indicia pattern could be chosen that would instruct the patient how to trim opposing sides to get correct measurements, trimming only one side. This would reduce the number of trims needed in fitting the garment. FIG. 16 shows a compression garment with opposing bands. In this embodiment, the bands can be trimmed by cutting along lines 1604, 1605, and 1606. The proper trim level for each level would depend on the patient's corresponding limb measurements for that level and the indicia printed on the garment. In this embodiment, the top band can be removed by trimming along indicia 1601 and the bottom band can be removed by trimming along indicia 1602 in order to properly fit the patient. Note that in this illustration it depicts markings and indicia where entire sections of the garment including bands can be trimmed away instead of portions of trimming away portions of appendages of the planar material. The trim-to-fit concept then applies to planar compression material, appendages, as well as to bands. The attachment mechanism may be sewn on the outside of the distal aspect of the bands or can be selectively detachable as in FIG. 11.

FIG. 18 depicts a planar compression garment with added padding. In this embodiment, the garment has additional low profile padded areas built into the garment. In the preferred embodiment, this additional padding would consist of sections of circular spacer fabric as manufactured by Beverly Knits of Gastonia, N.C. 1801 depicts padding which would extend around the ankle area of the garment and better protect the malleoli. 1802 depicts additional padding which may protect the tibia area by reducing subbandage pressure against the skin. Such an invention is useful for patients with sharp anterior tibial crests. 1803 depicts additional padded areas over the patella. Alternatively, if the garment was donned such that it would be closed in the front instead of the back, then 1803 would pad the posterior knee area, and section 1802 would pad the back of the calf. The padding may be permanently attached and shipped from the factory prior to fitting. Alternatively, the padding may be semi-permanently or permanently attached with fabric glue to adhesive or iron on transfers at the time of fitting. Alternatively, selectively detachable mechanism such as hook and loop or weak adhesive may be used. The outlines of 1801, 1802, and 1803 may be printed on the fabric so that the end user or fitter can take appropriate size padding and attach to the garment. The padding would then be included with the garment or as an optional feature that can be purchased separately. 1804 and 1805 show alternative shaped padding that can be printed as markings on the compression fabric. Alternatively, the padding may be attached in the center and can be trimmed to fit the correct size at time of fitting. As shown by the illustration, the markings and padding allow a wide range of solutions to be implemented either at time of garment manufacture or at time of fitting, or by end-user during acute phase edema reduction or for maintenance to prevent edema reaccumulation.

FIG. 20 illustrates for an arm garment the channeled padding patterns which may exist on the inner layer of the garment. FIG. 21 illustrates the channeling padding patterns which may exist for a leg garment. This channeling may be manufactured out of spacer fabric for highest breathability, comfort, and safely, but traditional foam technology is also possible.

The markings on any of the garments may be color coded, may have indicia, labels, or other identifying marks that help identify or determine which line the garment should be trimmed in order to provide the proper fit. In some embodiments, the markings are woven into the fabric, while in other embodiments, the markings are applied using an ink or dye. Such ink can be applied using standard silk screening or inkjet technology, as is known in the art. Furthermore, the markings may be permanent or may wash or wipe off, such that after customization to fit, the markings may be removed and would no longer be present on the garment. In some embodiments, the ink used on the indicia and markings would be fluorescent ink such that a black light is needed to see the trim marks and without it the indicia and markings are not visible to the patient. In some cases, a measurement form or table may be used to help guide the determination and help trim the garment quickly and effectively without error in order to provide proper fit and no markings would be needed. Guide patterns that overlay the garment and identify the trim lines also may be used. Other markings are also contemplated.

FIG. 3a shows an illustration of an arm wrap design using single piece of compression material. Note that multiple attachment mechanisms 1100 are shown on the arm. FIG. 3b shows the arm garment prior to trimming.

Joint Piece

Some embodiments of the garment would include a joint piece. The jointpiece may be a piece of the same compression material as one continuous garment, or may be made of separate materials. It is desirable to have increased longitudinal stretch ability in a jointpiece to allow proper limb movement. In some embodiments, the garment would have a section of material cut out of the middle of the garment and an alternative material or materials inserted. This may be desirable for proper fit. For example, if the garment is made of short-stretch material with 30% maximal elongation along the radial direction, the material might stretch properly if applied over the back of the elbow or the patella of the knee. In this case, high stretch compression material with 100% stretch or higher stretch might be provided to allow proper fit during joint flexion and extension. It is understood that the shape cut out and replaced might be a square, an oval, or a triangle, or other geometric shape. FIGS. 3b and 3c show an area where compression material is cut and replaced with high stretch compression material 5301. FIGS. 4a and 4b show a triangular area 5302 of high stretch material in the garment over the patella area. The joint piece might contain additional layers over certain areas to provide padding or comfort. For instance, it is common for compression sleeves to irritate the antecuboidal fossa of the elbow. Sewing in silk layer here or foam or spacer fabric padding, or choosing a softer higher stretch compression material might provide better fit to the patient.

FIG. 4a shows a thigh high embodiment of the garment. In this garment, the attachment mechanism 1100 are shown toward the back of the limb. Alternatively, the garment may be donned with the attachment mechanism anteriorly. 5302 shows an area of high stretch material over the patella. The garment may consist of a single planar sheet of compression material. FIG. 4b shows the thigh high garment prior to trimming. The garment is centered around the joint piece and then fit proximally and distally. Trim lines 4003 and 4004 are shown where the top of the garment can be trimmed to fit appropriate height. Trim lines 4001 and 4002 are shown where the bottom of the garment can be trimmed to fit appropriately the lower limb. A joint piece for the foot (not shown) may be included as part of the planar compression material or may be separate. Alternatively, a FarrowHybrid™ stocking may be used which provides compression distal to midfoot and as high as the ankle, giving a low profile foot piece.

In other embodiments, a jointpiece specifically designed to fit the joint in question may be used, and the compression material on the proximal and distal sides may be attached. FIG. 5 shows a diagram of such a compression garment. In this design, any joint piece design may be inserted into box 501 and sections 502 and 503 include the large planar compression material with designs as disclosed herein. Such joint pieces are disclosed as FIGS. 42-52 of previously filed U.S. patent application Ser. No. 12/391,051 filed Feb. 23, 2009 included herein for reference.

Additionally, the bands and/or spine may be made from both one way stretch and two way stretch. The two way stretch bands provide a softer end stretch over more sensitive areas such as joints, and allows for range of motion in addition to compression when used over joints. Thus, two way stretch bands may be preferable for use over joint articulation areas, whereas one-way bands may be preferable over non joint areas, as they are less prone to necking (shrinking in the middle when stretched).

Some embodiments of the garment for a jointpiece may include a mesh pocket which locates at the back of the knee when worn. This pocket provides for insertion and removal of selected padding pieces, such as a foam or spacer fabric insert, for better protection of sensitive parts of the back of the knee.

Trim-To-Fit Method

In another embodiment, a method and system are disclosed for providing custom and or customized garments to patients from off-the-shelf or trim to fit sizes/components based on limb measurements. This is explained further with reference to FIGS. 29-30.

Laplace's law dictates the correlation of leg circumference with compression level. For smaller limbs, there is more compression on a limb portion than for a larger limb given an equal tension applied. The width of the bands also is an important factor when determining the compression level. For more narrow garment sections applied with the same tension, there will be more compression on the underlying limb portion than if the garment appendages have wider widths. If the garment section is applied with the same tension to a limb portion with wider circumference, there is less tension per area on the underlying limb portion. Therefore, to accurately gauge the compression applied to the limb at rest, one must take into account the limb circumferential measurements.

Figure 29A:
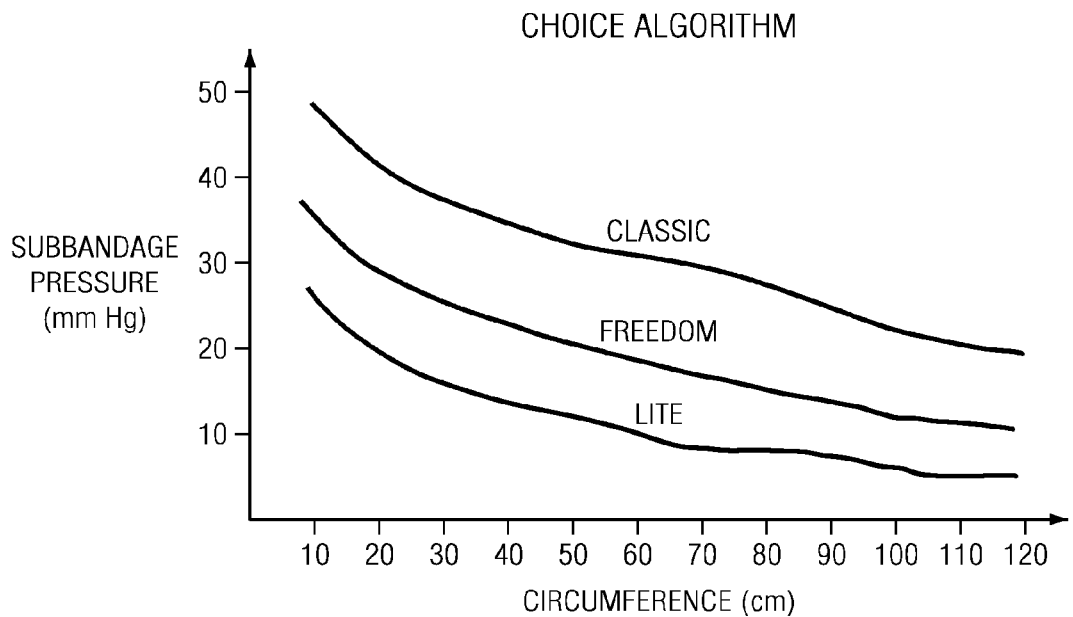
Figure 29B:
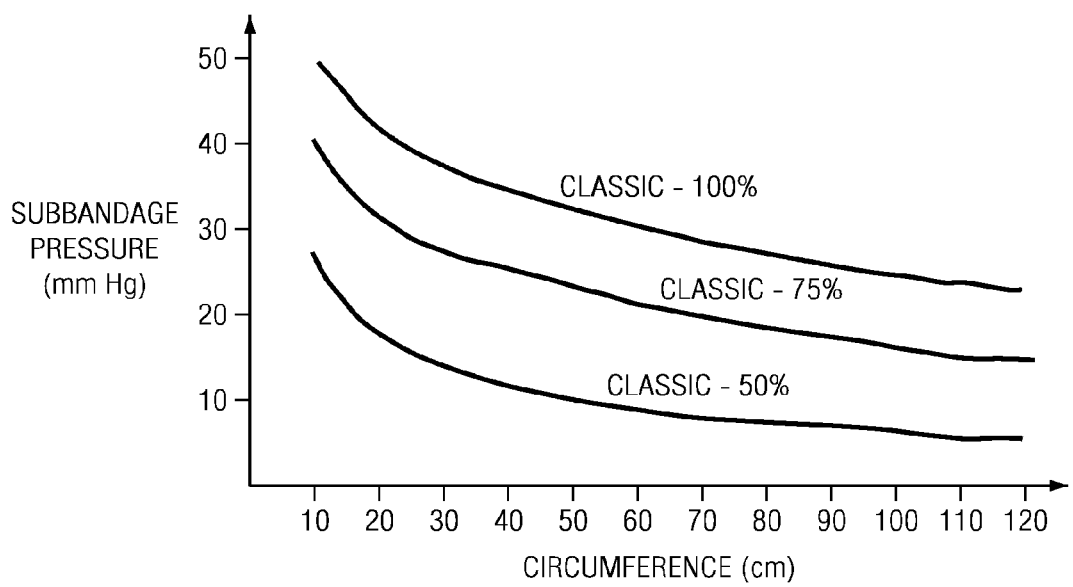

A form with instructions may be used for customizing the trim-to-fit garment. A user measures the actual circumference of an affected limb. Then, based on the type of material desired and the required compression level, a Choice Algorithm would help the user to select a correct product line. The Choice Algorithm graph, as shown in FIG. 29$a$ indicates the proper resting compression of different garment material types (along the vertical axis) for a given limb circumference (along the horizontal axis) when the garment section is applied at or near end-stretch for a short-stretch material. The compression levels would be different, depending upon the type of material chosen allowing for choice when prescribing the resting compression level. The garment section compression rating includes variations due to Laplace's law, which states that compression differs with limb circumference. In this example, these are short-stretch garments applied at or near end-stretch. In other embodiments, these may be other band types: nonelastic, long-stretch, medium-stretch. One can use similar algorithms for maximal stretch (100% stretch), 75% maximal stretch, 50% maximal stretch for a given elastomeric stretchable material, for example, as illustrated in FIG. 29$b$. Other possibilities exist as well. Instead of displaying the subbandage pressure, the Choice Algorithm may display the Skin Surface Pressure and take into account the type of padding in the garment. For example, a garment section applied over a thick foam liner with 1" of foam would provide less Skin Surface Pressure than a garment section applied over a very thin 2 mm thick foam liner. Thus, the user can use a simple chart to correctly select which padding type and garment type to use for a given clinical application and desired therapeutic compression range.

Figure 29C:
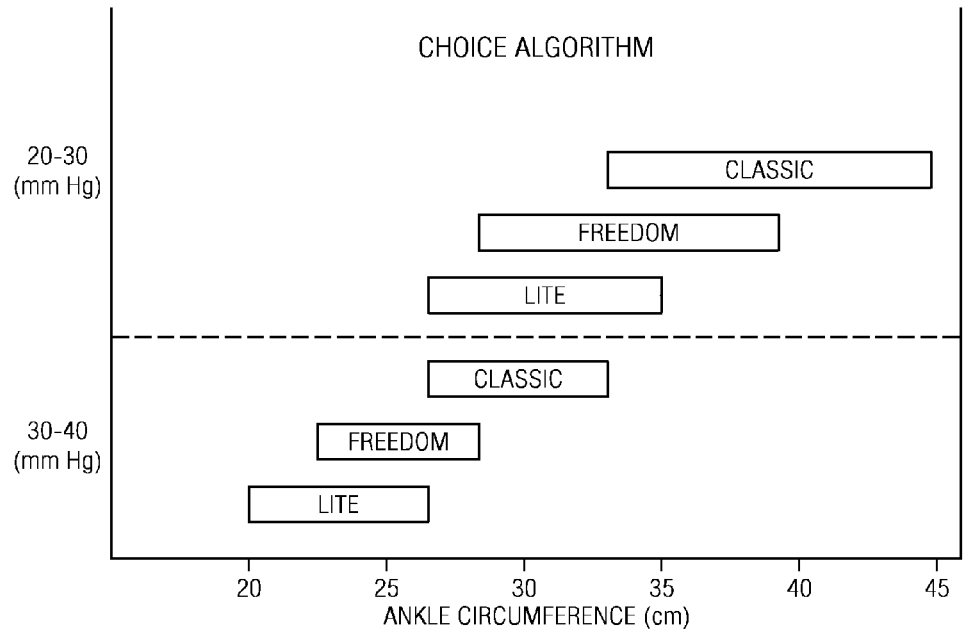

FIG. 29C shows another embodiment of a Choice Algorithm. In the United States, most compression garments have a compression rating that lies in the ranges of: 8-15 mm Hg, 15-20 mm Hg, 20-30 mm Hg, 30-40 mm Hg, or 40-50 mm Hg. Most practitioners are used to prescribing a range of therapeutic compression, with the understanding that of-the-shelf garments provide this compression range over a range of limb circumferences. The rating system typically has the most compression at the wrist or ankle, with less compression proximally so that graduated compression is provided. Short-stretch products as illustrated in this invention may or may not provide graduated compression, as this may in certain cases be less important for garments applied at or near end-stretch. It is understood for garments sold in other countries such as Europe, the garment would use a British standard, German standard, or French standard, for example instead of the US compression ranges. The garments materials and design would be altered to provide correct compression ranges using these countries compression standards, or other standards that are known in the art.

FIG. 29D illustrates a Color Indicia System for different ranges of compression. Since 15-20 mm is generally safe except for severe peripheral arterial disease, it was given the color green. As the compression increases, the colors change to reflect more compression and therefore more caution. Red for instance, is often associated with stop lights, stop signs, or thermometer temperature level, as well as blood, and in this case represents higher intensity compression. The colormap shown in 29D may be used in any of the Choice Algorithms or bands to indicate general compression application. The colormap, for example, may be printed on the bands and reflect quickly the general compression level (safe to high intensity) either alone or in conjunction with other indicia. Other colormaps or ranges are possible, for instance using French or German Raul compression ranges, which are different than those commonly used in the United States. For the lower extremity garment pictured, additional color indicia may be added to show compression ranges. It is understood to one knowledgeable in the art that there may be different colormaps even on the same garment section, depending on the circumference measurement. Such color indicia may provide safety factor as well in helping the person trimming quickly double check compression ranges (make sure there are no red indicia if applying this to a patient with moderate/advanced peripheral arterial disease, for example).

For FIG. 29C, the color indicia may be used to provide color to the rectangles, which show the compression rating for certain circumferences. Since lower extremity compression garments are generally rated by the least ankle circumference compression rating, this chart shows the compression level ratings. Note that in this example, the same product can provide 20-30 mm or 30-40 mm compression, depending on the circumferences to which the product is applied. By mixing the garment composition, garment appendage width, considering the circumference of the limb portion at that limb level (in order to adjust for Laplace's law), many different combinations can be created to apply proper therapeutic compression levels, yet the details of all these many complicated variables remain hidden to the user, who gets a simple system to help them safely and reliably apply the correct compression level to the patient and correctly select the band materials or product and trim garment appropriately. Additionally, in some embodiments additional compression may be added to certain garment sections. In the cases of edematous lobules, for example, the principle in bandaging is to lift and compression this edematous lobules to decompression them. In the case of the single sheet compression garment, additional compression material could be added to reinforce the garment over the base of a lobule and provide higher compression. FIG. 19 shows a planar compression garment with added material 1901, 1902, and 1903. These various geometrical shapes are designed to help pull upward on the garment to lift and compress a large lobulated area above the knee. Such large lobulations are often seen in Lipedema, lymphedema, and especially severe Lipolymphedema patient populations. Additional geographic shapes are possible. These compression materials can be added at time of order for a custom garment. Alternatively, they can be provided as separately purchased material or come with the garment. These compression materials may be sewn in place, glued with fabric glue or adhesive, or may be iron on transfers or other attachment mechanisms as known in the art. These extra compression materials help reinforce problematic areas and they can be used to change the direction of the compression vector to provide additional therapeutic effect.

Additionally, extra spine material may be trimmed out just below the lobule to make the garment fit tighter up underneath the garment and form fit. The spine material may be trimmed along indicia as shown in FIG. 17.

An indicia system can be drawn on, sewn in, or otherwise associated with the garment, telling the user where to cut the garment for a given circumference in order to get the correct garment length for the desired compression. One example of this is to create a compressed scale. For example, a limb measuring 100 cm in circumference may be treated with a 50% maximal stretch short-stretch garment. When applied at end-stretch, the garment would apply, for example, 30-40 mmHg range resting compression over a range of circumference limb portions. The garment may contain an indicia system with simple numbers, telling the user to cut the garment there. Since the garment only needs to be 100 cm/150% long to be applied at end-stretch, the indicia system would tell the user to cut the garment at a point slightly longer than the 66.67 measurement. Because of possible user error and prudence to leave room for the garment to work even with some leg swelling, the corresponding indicia for a 100 cm limb at points would be put such that the user would cut the unstretched garment appendage off at 75 cm in length. This point would be 75/2 out from the middle of the garment, which is 37.5 cm from the midpoint on either side. At this location on either side of the garment, the indicia would say 100 or 100 cm or something similar. There would be similar indicia for other limb measurements of 90 cm, 110 cm, etc. such that the user would know where to cut to make the garment the proper length to provide the desired compression to a limb.

The method includes taking measurements of limb sections, then using an algorithm which takes into account the stretch characteristics of the material, to figure out what length to cut the garment. The algorithm takes into account the maximum stretch of the material and tells the user what unstretched length to cut the garment appendage. This measurement would be made outward from the midpoint or include a double ruler which has middle as the zero point and counts up on either side. Also, the garment appendages could in some embodiments be cut at the actual circumference measurement of the limb for greatest intuitiveness. For some embodiments such as the arm garment of FIG. 3b, the garment is asymmetrical by design and the measurements would be from the edge of the garment or from some indicia printed on the material.

Preferably a disposable or reusable ruler would be used which would tell the user where to cut each band. For different compression levels, there would be different algorithms. For example, one compression band may have maximum stretch of 50%. The compression when applied at end stretch to one ankle size may be 40 mmHg, or some other predetermined compression amount. The ruler would tell the user where to cut the bands so that when they are overlapped, the band applies a compression level of, for example, 40 mmHg at or near maximal stretch. In another instance, we may want to use the same garment to only provide 20 mmHg compression. In this case, the compression at half maximal stretch would be 25% stretch and may correlate to 20 mmHg. Another ruler or indicia would tell the user where to cut the band such that when overlapped on the limb the band applies a correct compression level of 20 mmHg.

To elaborate on this concept, we give the formula below which helps the manufacturer develop a compression ruler or indicia system which takes into account all the variables. This indicia system created may be printed on a disposable paper double ruler included with the product or a reusable ruler, or as indicia printed on the band, to name just a few methods of relaying such information. In one example, compressed length markings are used on bands that consider the amount of stretch and desire to leave some lateral overlap at each band level (ex. 20-50% overlap after garment applied correctly). The user would measure the actual limb circumference and cut along the markings/indicia on the band(s) that match the measured circumference. The user may use an optional measurement guide and instructions such as provided in FIG. 55 to assist with proper measurements at each band level. This could be a direct 1:1 relationship or some other relationship. For a 1:1 relationship, the user would measure the limb circumference, and then cut each band the same length as the circumference of the limb measured for that limb level. For a better fit, however, a formula could be used to create a compressed length at which each unstretched band should be cut. This compressed ratio would take into account the degree of stretch at application of the garment, and perhaps include a fudge factor in case of diurnal variation in swelling, mismeasurements, etc. One example of this compressed ratio would be as follows: The limb measures 100 cm in circumference at a level. The band is a short-stretch band with 50% maximal stretch. The length of the band once applied at maximal stretch would be as follows:

$$BLn = ((LMa + PL)/(1 + BSA)) * (1 + PBOd)$$

where BLn—Band Length Needed for that limb level, LMa=actual Limb Measurement at that limb level, BSA=Percent band stretch at application, PBOd=Percent Band Overlap desired, and PL=Padded Liner extra circumference at that limb level.

For this application $BLn = 100/1.5 = 66.67$ cm. The Percent Band Overlap desired is perhaps 20%, as we want to include extra length for possible measurement error and leave room for the garment to still work if patient's limb swells 20% over the circumference measurement at the time of fitting/trimming. In this case the patient will be using a sock type liner under the wrap, so the PL will be negligible and estimated at zero. If there were a padded liner used on the limb, the PL would add the additional circumference of the padded liner to that limb portion to the calculation. If the measurements of the limb LMa were done over a patient with the liner already applied, then PL would be zero for all calculations as the LMa would already include the extra circumference of the padded liner. In this case, the compressed scale would have actual length of 66.67*1.2 or 80 cm. So for this compressed scale example, we would want the band at this band level cut to have 80 cm total unstretched length for proper fit.

The compressed indicia system can be done several different ways in order to make it easier to trim and fit the garment for the user. One way is to print a compressed scale indicia on the garment. Another method is to use a double zero ruler which the person fitting would use to trim the band appropriately. This may be the end user, a medical professional, a hospital personnel, or a person at a Durable Medical Equipment store. The compressed scale would tell the user to cut the garment appendage length 80 cm (40 cm on either side of the midpoint) by using some type of indicia. In this example, the printed number may simply read "100" or "100 cm" at garment section 40 cm from either side of the garment midpoint. By calculating and printing indicia at regular intervals (every 5-10 cm for example using the compressed scale), the user would simply measure the limb at each appendage level and then cut at the location closest to their actual limb measurement. The built in scale will have done all the calculations in order to reduce risk of user error and make trimming as simple and uncomplicated as possible.

In some embodiments, a chart may tell the user exactly where to cut the garment appendage to achieve 100% maximal stretch for the first line of the chart, 75% maximal stretch for the second line of the chart, and 50% maximal stretch for the third line of the chart. Since the garment would be trimmed to exactly correct length, the user would apply the garment with exact specified compression, even if not applied to end-stretch. For example, if we want a user with moderate peripheral arterial disease and diabetes with neuropathy to apply a Classic garment, we may use a chart with indicia to trim the garment at 50% maximal stretch, in order to provide 15-20 mm compression at the ankle. This would provide a safe therapeutic compression level for this patient, even though garment is not applied at end-stretch. For a different patient who has no peripheral arterial disease but has severe lymphedema, we may use a chart to trim the garment to fit at 100% maximal stretch to provide 40 mm end-stretch compression at the ankle and maximize the calf-muscle pump as well as prevent any additional swelling, since the garment section is applied at end-stretch. Thus the chart provides another method of taking complicated variables and summarizing them in a simple and reliable method to make a one-time change to the garment which will permanently change the fit and performance characteristics of the garment, depending on patient's limb sizes and desired performance characteristics.

For another application, the chart may indicate where the user should trim the garment sections to provide a predetermined compression level (for example 30-40 mm Hg range compression). In this case, the chart would take into account the degree stretch of the garment material type in order to get the proper level therapeutic compression.

For a padded liner, the compressed scale in some embodiments would already consider the extra length needed for the garment, depending on the application. For example, a padded liner in one embodiment may increase circumferential measurement of a limb portion such as the Least Ankle Circumference by 4 cm. Therefore for the following example PL=4. In this example, we will use a short-stretch garment material with 34% maximal stretch and use the formula to properly size a garment section around a 27 cm ankle. We will include just 5% overlap, so POd will be 0.05. In this case, the calculation becomes: $BL_n=((27+4)/(1+0.34))*(1+0.05)= (31/1.34)*1.05=24.29$ cm. For a 73 cm thigh measurement with PL of 6 cm and desired overlap of 10%, the calculation would be $BL_n=((73+6)/(1+0.34))(1+0.1)=(79/1.34) *1.1=64.85$ cm. Thus, by building in the desired padding, and knowing the percentage stretch of a short-stretch material, a system can be built so the user can easily and with low error correctly trim a garment to properly fit a limb portion.

Similar calculations can be used for any stretch material. In some embodiments, the indicia lines may be marked with the compressed scale in order to show the person trimming the garment how to trim it to properly fit the limb. Other indicia line types are possible for other limb segments, and indicia may reflect something simpler for the user such as trimming along indicia which vary depending on the patients pant length or waist length or shoe size or other type markings (small, medium, large, for example).

For different types of materials, there may be different amounts of stretch. Choice algorithm FIG. 29A shows a representative graph of different pressures of short-stretch garment materials applied to different circumference limb sections. All points are for garments applied at end-stretch. The user could look at the circumference of the limb portion and the desired compression level the healthcare practitioner wants to apply, and select the proper material type to use. In FIG. 29A, for instance, a 40 cm circumference ankle would have about 15 mmHg resting compression for the LITE, 25 mm for the Freedom, and 35 mm for the Classic when applied at or near end stretch. In one example, the patient has diabetes with moderate peripheral neuropathy and some Peripheral Arterial Disease, but still needs lower extremity compression. In consideration of the patient's comorbidities the health care practitioner may select to prescribe the LITE material for the patient. In another example, the patient has good blood flow and severe lymphedema with ankle measurement of 40 cm. In this case, the health care practitioner would want heavier compression and would select the Classic, with 35 mm Hg resting compression on the ankle area. Thus the practitioner could stock three different versions of the trim-to-fit garment and would only need one size of each version to apply a highly customized solution with highly predictable and highly reliable compression levels that are appropriate for that patient's medical condition.

For selection of garments for use over the padded liner, the skin surface pressure on the limb will be different. The skin surface pressure we will define as the pressure on the outermost layer of skin. Therefore, the Choice algorithm would look different depending on the liner material and thickness and construction. These figures could in some embodiments give the correct Skin Surface Pressure, rather than the Sub-Bandage Pressure. In this case, the Choice Algorithm would have lower mmHg reading built into the scale (giving correct skin surface pressures rather than subbandage pressures), to aid the practitioner with proper selection of garment materials in order to provide proper therapeutic compression. It is important to note that the skin surface pressures measured also depend on tissue softness. This means a posterior calf skin surface area would be lower due to softer underlying tissues than a reading over the anterior tibial crest, which is quite bony. All these considerations can be built into the correct scales to make a solution that is as simple and seamless as possible for clinician, technician, and patient.

Figure 30:
FIG. 30 is an illustration of a Choice Algorithm table.

Alternatively, the indicia showing where to cut may additionally or alternatively indicate the resting compression level applied to a specified circumference when applied at end stretch. FIG. 30, for example, shows garment cross-section with up to three compression ratings XX-YY-ZZ where XX is resting compression level at maximal or near maximal material stretch, YY is resting compression level at 75% maximal stretch, and ZZ is the resting compression level at 50% maximal stretch. These ranges were chosen in particular because users can determine not only the maximal end-stretch of short-stretch materials, but some general range of maximal stretch as well with reasonable predictability and reliability. By selecting the correct size and trimming correctly, the proper compression level for a given circumference can be determined by the user. These indicia may contain additional colormaps or use colormap blocks instead of numbers in order to indicate ranges of compression. One benefit of such a system is that this needs to be determined only once at time of garment selection and trimming, then the garment can be given to the patient and the patient can reliably and predictably apply the garment with correct and safe compression levels and have a properly fit garment. In this example the garment section cut along the 30 cm line (which could represent actual measurement or a compressed measurement as described by equations above), the user would get resting compression of XX1 mmHg compression if the garment section was applied at maximal stretch. If applied at 75% maximal stretch, for a 30 cm garment section length the user would get a resting compression of YY1 mmHg. If the user applied the garment at 50% maximal stretch for a 30 cm garment section, the user would get a resting compression of ZZ1 mmHg. Thus, the current invention proposes a correct rating system of compression to determine actual subbandage pressure or skin surface pressure of a garment. The compression rating system could similarly include different ratings depending on the padding selected or other criteria.

Such a system has clinical benefits. For example, as a lymphedema patient wears a Classic garment that provides 40 mm resting compression to the ankle at a given diameter 35 cm in circumference. The patient is to undergo surgery elsewhere on the body. Because surgery often involves fluid fluctuations due to IV fluids, blood loss, blood pressure fluctuations due to analgesia, etc, some patients get significant worsening of their lymphedema. At the same time, it is the author's experience that greater than 20 mmHg resting compression for a surgical patient may be dangerous because of anesthesia causing lower blood pressure and perfusion pressure, analgesias on board etc. At the same time, lower extremity compression is necessary and useful to lower incidence of deep venous thrombosis. Therefore, by utilizing the rating system, the correct compression for maximal therapeutic purposes and maximal safety may be 20 mmHg end-stretch. In this example, the patient may look at their garment and note that at 35 cm their compression rating is 40-30-20. In this case, the patient understands they can apply their garment at 50% maximal stretch and get 20 mm compression to their limb, even thought it is not applied at end-stretch. In this case, their garment with 20 mm compression would certainly be safer than wearing no garment at all (which would increase risk of blood stasis and DVT formation), and safer than wearing a 40 mm garment during surgery.

In other embodiments, the indicia may be linked to the amount of internal compression applied to the tissues inside the limb portion, which is different from the surface compression applied by the garment either with or without a padded liner. Thus both the practitioner and/or end user would know both the external compression generated as well as the internal compression to the limb as both could be printed on the indicia.

It is important to consider hand strength necessary to pull bands to appropriate tension. Most doors are rated to open with pulling strength less than 5 lbf of force. It is desirable, therefore, that the bands be configured such that the tension needed to pull the bands to near or at end-stretch lie inside a range of 1 to 10 lbf. In some preferred embodiments, the desired tension lies within a more narrow range of 3-5 lbf. The amount of tension to achieve the compression could be varied by narrowing the garment appendages in order to keep required hand tension within an acceptable range, while providing a garment with the correct amount of therapeutic compression to the underlying limb. Lower required pull forces are preferable so that patients with less hand strength can still apply the garment correctly and with reliable and predictable compression levels.

For far more elastic (beyond 100% stretchability) garment materials, geographic markings (rectangle-square or oval-circle) may be used with appropriate stretch and then trim-to-fit markings Squares may be placed on the device at the proper stretch ratio that would generate the requisite compression on the circumference that the garment is trimmed for. This way, a trim-to-fit garment could be made to properly fit for a material not applied at or near end-stretch. For short-stretch bands, these indicia may provide additional confirmation the garment was applied correctly for best fit and function and additional safety factor.

Any embodiment presented above with ruler, chart, or print-out on the garment may be used. Also, a built in 20-50% compressed ruler may be used for the customer to cut garment appendages such that there would be a fudge factor built in to allow for some user error, swelling fluctuation, etc.

FIGS. 12 and 13 show an embodiment of a legpiece of the current invention using a trim-to-fit design. In this exemplary embodiment the legpiece is an off-the-shelf legpiece that is customizable at the point-of-sale such that the patient would be provided with a custom garment having a proper fit and proper compression levels and gradients at the time of the patient's visit. The legpiece may be made from a single piece of material without the need for individual bands. This legpiece may be made from unidirectional wrap and may have a trapezoidal or other shape that would best conform to the patient's leg and that would overlap on the anterior portion of the leg.

The legpiece would have markings, such as lines and other indicia, on one or both sides to indicate locations where the legpiece may be trimmed to accommodate the patient's leg length, also markings for trimming to the patient's leg circumferences at locations along the leg length, and markings for locations where slits may be cut.

The indicia locations for trimming to the patient's leg length would be in a 1:1 correspondence with the patient's actual leg length measurement.

The circumference indicia at predetermined locations along the patient's leg length may be pre-calculated according to an algorithm so that when donning the legpiece would provide proper compression for each circumference along the leg length. An actual measured limb circumference of the patient would correspond to a likewise numbered indicia on the legpiece. However, the actual length of the measured leg circumference and the actual length on the legpiece indicated by the circumference indicia may not be equal. This would facilitate proper compression at each particular circumference along the leg length as the legpiece is wrapped around the limb and attached at corresponding indicia locations. Other markings would indicate where slits may be cut. The slits markings would be between 2-3 centimeters long, however, other lengths may be used. This would allow for sufficient overlap to properly secure the legpiece to the leg, provide proper and safe compression levels to the leg, and prevent the occurrence of windowing, exposing areas of the limb. Exposed areas may reduce the effectiveness of the treatment because those areas would receive no compression. This design would have superior conformance to the patient's limb shape while alleviating the need for angular bands. Because the legpiece is made from a single piece of material, the manufacturing process would be greatly simplified and accelerated. Also, the cost of manufacturing would be greatly reduced.

The bands are shown angled downward. This is because the limb portion tends to decrease in circumference more distally and is shaped somewhat like an inverted cone. Angling the wrap downward allows the appendages to provide more uniform compression along the width of the band and can help reduce garment slippage. For a trim-to-fit embodiment, it may be useful to provide multiple angles where the band can be cut. This allows the person fitting the garment to select which angle is needed to best fit the limb. For limbs with a fast rate of change from large diameter proximally to a smaller diameter distally, cuts along steeper slopes 1203 and 1204 might be needed. For limbs with a slower rate of change from proximal to distal, a slower slope rate like 1203 and 1205 might be needed.

To provide proper angling at the proximal-most end, indicia can indicate where to trim the spine along 1201 to remove a dart shaped piece of material. This would give the top of the wrap a more concave shape above the calf muscle and allow the compression vector to be more axial. Please note that only one dart line is shown here, but smaller or larger darts may be needed, depending on the angle chosen for the bands. In other embodiments, three or more dart sizes may be drawn. The cut lines may be color coordinated or have other markings to show which cut lines are parallel to their more proximal and distal counterparts. In some embodiments, a slow angle cut may be needed at one portion of the limb and a sharp angled cut at a different portion of the limb. A measuring selection guide can help the end-user determine which of the angles and dart line they should cut along.

Alternatively, for custom garments a computer program could receive all the measurements from the limb, decide which markings and cut lines are indicated, and print these on the planar compression material with a CNC inkjet and cut the garment out with a CNC cutter. This would allow computer entry of the limb measurements and an output which is the custom garment with appropriately marked and cut locations. The attachment mechanism could then be attached and the garment would be ready for the patient with low cost and quick process time to make the garment.

Method for Graduated Compression

Graduated compression is desirable for many garments. While some experts question whether graduated compression is needed for short-stretch garments applied at or near end-stretch, for garments applied not at end-stretch graduated compression is helpful for edema control. Herein is disclosed a method for providing granulated compression in a trim-to-fit garment. For the graduated compression planar trim-to-fit compression garment, more narrow cuts would be done distally. Each cut would result in an appendage from which an attachment mechanism would be used on the garment. By placing the cuts closer together distally, there would be additional compression vectors to this limb section. Proximally on the garment, the compression vectors would be spaced further apart due to wider appendages. The result is less compression per surface area on the wider appendages, assuming each appendage is pulled with equal strength. Thus, graduated compression can be applied to the garment. By placing indicia and markings, the cuts to create the appendages can be altered in location in order to create proper graduated compression.

Figure 22:
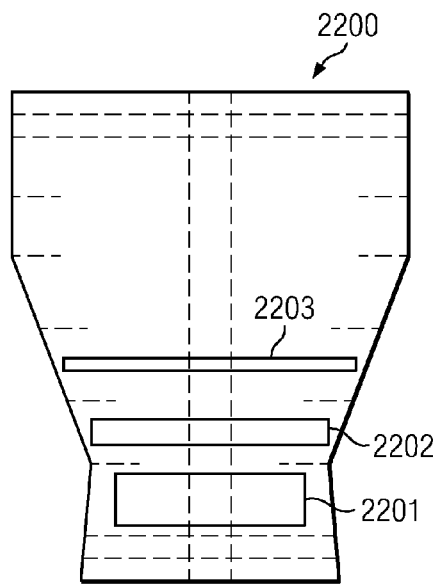
FIG. 22 is an illustration of a compression garment with graduated compression due to added compression material in the design.

As an alternative, extra compression material as shown in FIG. 22 could be used across the diameter of the garment, providing additional tension and thus a stronger compression vector. There would be smaller amounts of extra compression material as the garment moved proximally. In this embodiment shown, one wide piece of compression material 2201 provides additional compression on the distal-most band. The more proximal bands have smaller additional compression material 2202 and 2201. Other geometries of added compression materials are possible. This additional compression material can be added to the inside or outside of the garment using one of many different attachment mechanism.

Figure 23:
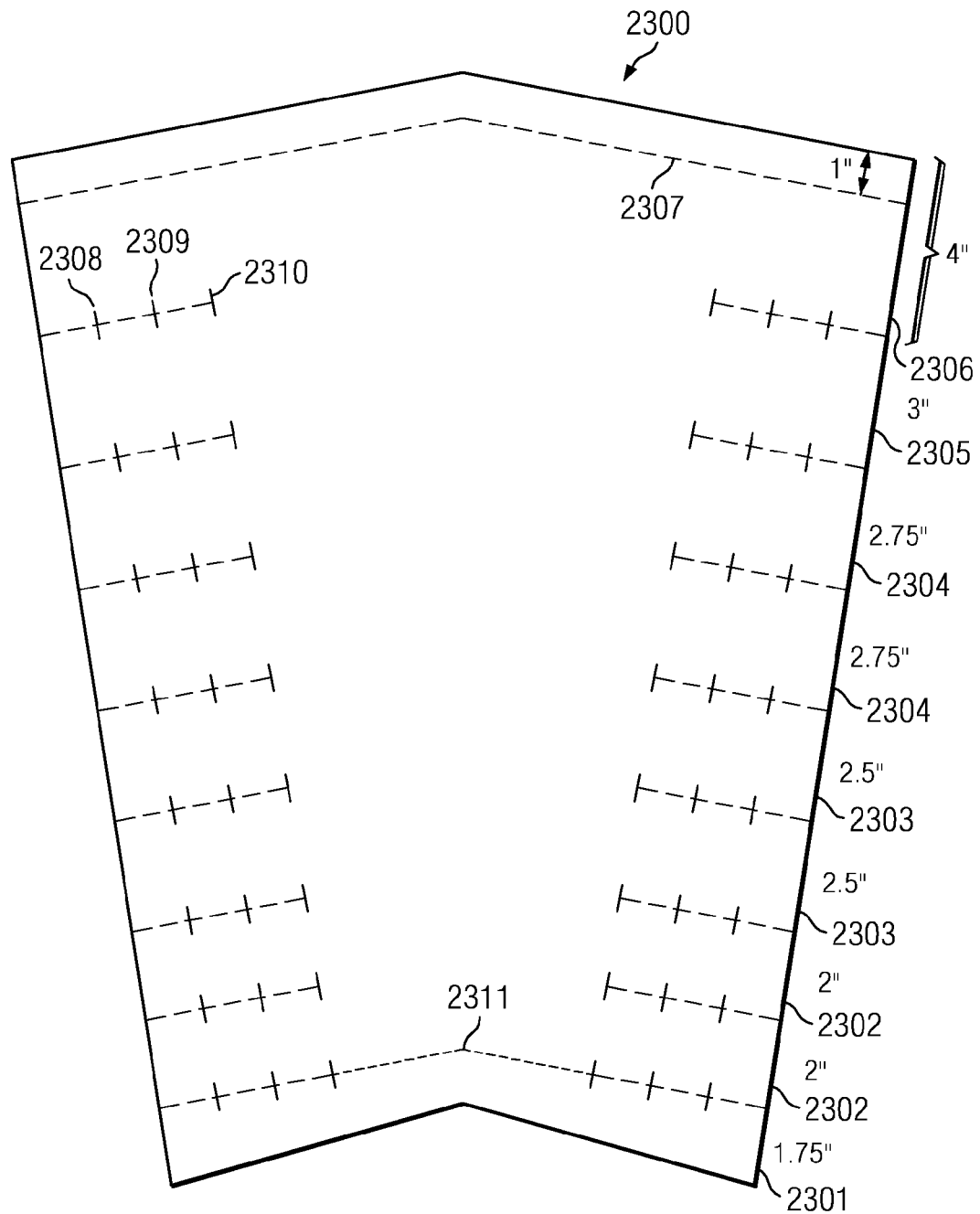
FIG. 23 is an illustration of a compression garment with graduated compression.

FIG. 23 shows an embodiment of a garment with graduated compression. The more distal appendages are trimmed back along the cut lines according to the indicia and patient's measurements. The indicia can be a 1:1 ratio to actual measurements or another ratio as disclosed by the formula disclosed herein, and previously discussed in U.S. patent application Ser. No. 12/391,051 filed Feb. 23, 2009. The cuts made distally define the lower appendage 2301. For a short limb section, this can be trimmed away along trim line 2311, which is an extension of the cut line. More proximal bands gradually become wider. For cuts 2302, the second and third appendages have widths of 2" wide in this example. For cuts 2303, the 4th and 5th appendages have widths of 2.5". This continues for cuts 2304 where the bands are 2.75" wide and then cut 2305, which creates a 3" appendage and a 4" appendage at the top. For a short limb, the top 1" may be trimmed off the top appendage to create two 3" appendages. The garment is then trimmed back along the indicia 2308-2310 depending on the patient's measurements. The result is a garment with graduated compression, as each appendage and its attachment mechanism create a corresponding compression vector. The higher density of distal compression vectors means there is increased compression distally.

Method for Padding Applied to Garment

By using a form, the end user or business or clinical person can fill out the form to select the correct area(s) to be padded and the correct height of padding. The user can further select the correct thickness or layers of padding, type of padding, and whether padding was waffled, ribbed, or provided directional flow. This form may then be submitted to a manufacturer for custom manufacturing of the desired garment. The same technology used to print the indicia may print out the size, shape, and type of padding that needs to be applied or could be applied. This could streamline manufacturing by guiding production that this particular garment needs padding in certain location(s), or provide an DME or practitioner or end-user with the proper location to add or replace padding. The padding may or may not come with the garment at time of sale.

In another embodiment, a lymphatic flow system may be incorporated into or form a compression garment. FIGS. 24-27 and the following paragraphs provide additional aspects of this concept as originally introduced and discussed as 1904.

Kinesio taping is known in the art. Kinesio tape is a tape which can be cut and attached to the skin. It is a single use device which is a single use disposable. It is used in sports medicine and lymphedema and chronic edema. The mechanism of action is thought that the tape provides a push-pull action on the superficial lymphatics in order to improve lymphatic flow. The tape can be stretched as it is applied to the skin, so that it provides some buckling as it shrinks This buckling is felt to push and pull on the skin, activating the lymphatics under the affected area, and possibly activating afferent nerves as well.

Other chipped foam garments such as the Jovi Pak, Solaris Tribute, and similar products provide large padded foam garments with channeling to mimic lymphatics. These foams are meant to provide high and low compression areas and also may help activate superficial lymphatics to improve swelling.

Accordingly, in another aspect of the current invention, a padding material is designed to be used with compression products. The padding material is designed to be superior to chipped foam garments and simpler to apply than kinesiotaping. In one aspect of the invention, there are geometric shapes which provide channeling of lymphatic flow. In another aspect of the invention, the design of the material can include a geometry to help recreate and maximize the push-pull effect which can improve circulation of the skin and reduce swelling and improve healing. This material may be sewn into a planar compression product such as that disclosed herein, or provided as a stand alone product that can be used under compression bandaging, compression stockings/sleeves, or multilayer compression wraps. This garment can provide similar push-pull on lymphatics as Kinesio taping, provides a greatly reduced footprint compared to large bulky chipped foam garments, and may be provided for a fraction of the cost. Additionally, the material can be applied with less cost since it requires less application time and less training is required.

Figure 24:
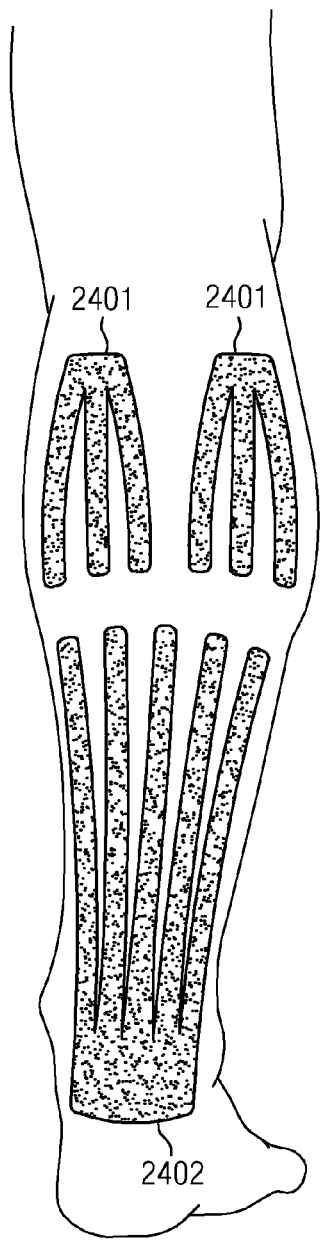
FIGS. 24-27 are illustrations of various embodiments of geometrically arranged padding.

FIG. 24 shows the back of a calf. In this figure, three separate foam or spacer fabric geometric patterns are illustrated. These patterns 2401 and 2402 are fern-like or fan-like in shape. The material may be 0.1-1 cm thick polyethylene or polyurethane open cell or closed cell foam or spacer fabric, although other compressive material can be utilized such as neoprene, breathoprene, or gel polymer type material. Other materials are possible. This material may be laminated to fabric on one or both sides. The lamination may be hook and loop compatible material. Alternatively, an adhesive backing may be used on one side to adhere to the skin. Different shapes and sizes of this product can be manufactured, and applied to the skin area. This may be a reusable, semi-reusable, or disposable product. It can be sewn or glued or cooperatively attached to the planar garment, or can be a stand alone product which can be used in conjunction with a trimmable garment, compression stocking or sleeve, or compression bandaging (either short-stretch lymphedema bandaging or disposable multilayer compression bandaging), as is known in the art.

Figure 25:
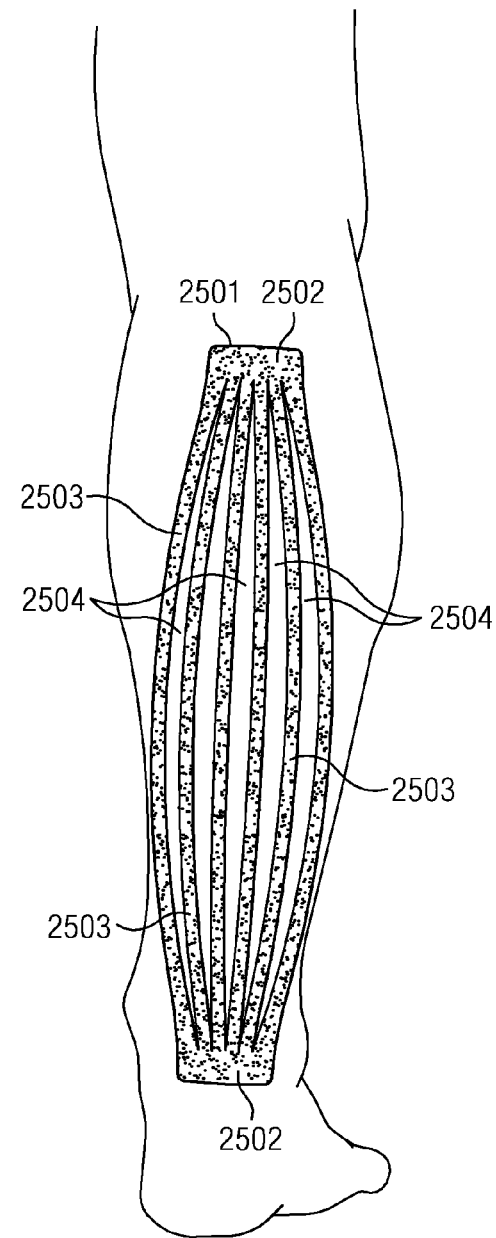

FIG. 25 shows another embodiment of the current invention. In this embodiment, the material has fan-like slits cut out of it. Please note that 2501 is a planar or cylindrical material that has been cut out or molded to have these slits. The material has fan-like anchors 2502 at both ends with finger-like projections 2503 which interconnect. Between the interconnecting areas are spaces 2504. The material can help channel superficial lymphatic flow in order to improve circulation to a body portion.

Figure 26:
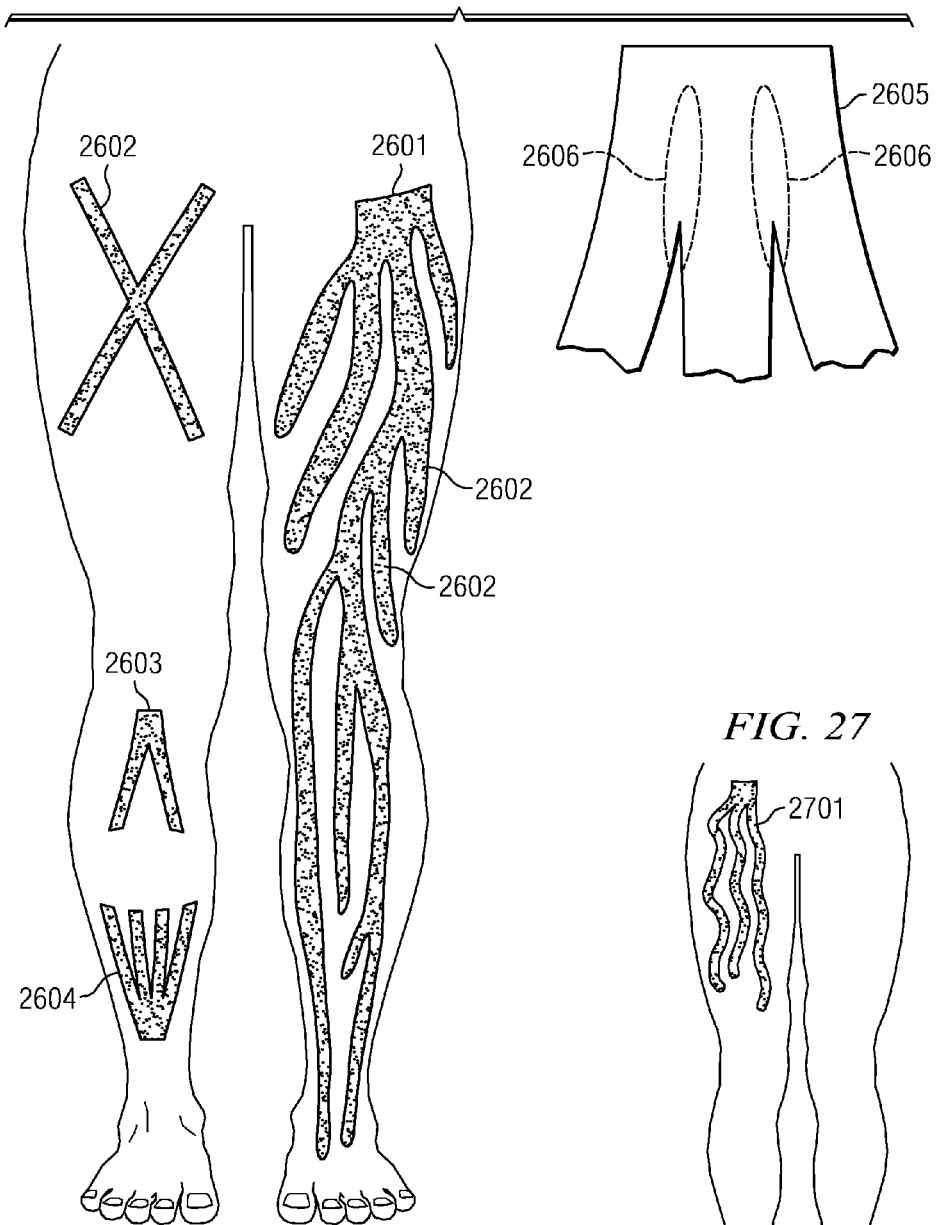
Figure 27:
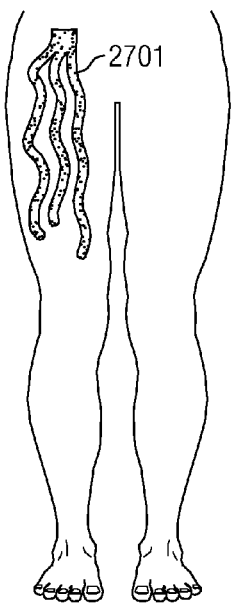

FIG. 26 shows more embodiments of the current invention. Embodiment 2601 shows a fan-like base proximally, with finger-like projections which branch. These branches 2602 may be symmetrical or asymmetrical and may have single or multiple branches in order to channel lymphatic flow and improve circulation and reduce swelling to the body portion. Embodiment 2602 shows an example of an embodiment with an X-shaped configuration. The material may have an X-shaped configuration in order to provide support to a body portion or improve circulation to a body portion. These configurations are used more in support of musculature, but can also improve circulation and reduce swelling. Embodiment 2603 shows a Y-shape material. Embodiment 2604 shows a fan-like shaped material. 2605 shows a close up of the base of the fan. In the case of using foam or spacer fabric, the base of the fan may have recesses 2606 which receive the foam. These recesses 2606 may pass all the way through the base of the fan, or may start with deeper recess distally which recedes toward the base of the fan. It is understood that other recesses or channeling can be molded into the material as desired, and is not limited to this single illustration. FIG. 27 shows embodiment 2701, which shows fan-like base with finger-like projections which are wavy. The waves may vary in curvature depending on the body portion it is supposed to be applied to. The waves between different fingers may be same or opposite, providing symmetrical or asymmetrical waves, as desired.

The material may in some embodiments have a tape backing to adhere to the skin. The chosen adhesive may be sprayed on the material at time of use or may come with peel and stick type backing. The adhesive may be solid or applied in a matrix or other geometric pattern to improve breathability, as is known in the art. The adhesive may be thermally activated.

Figure 28A:
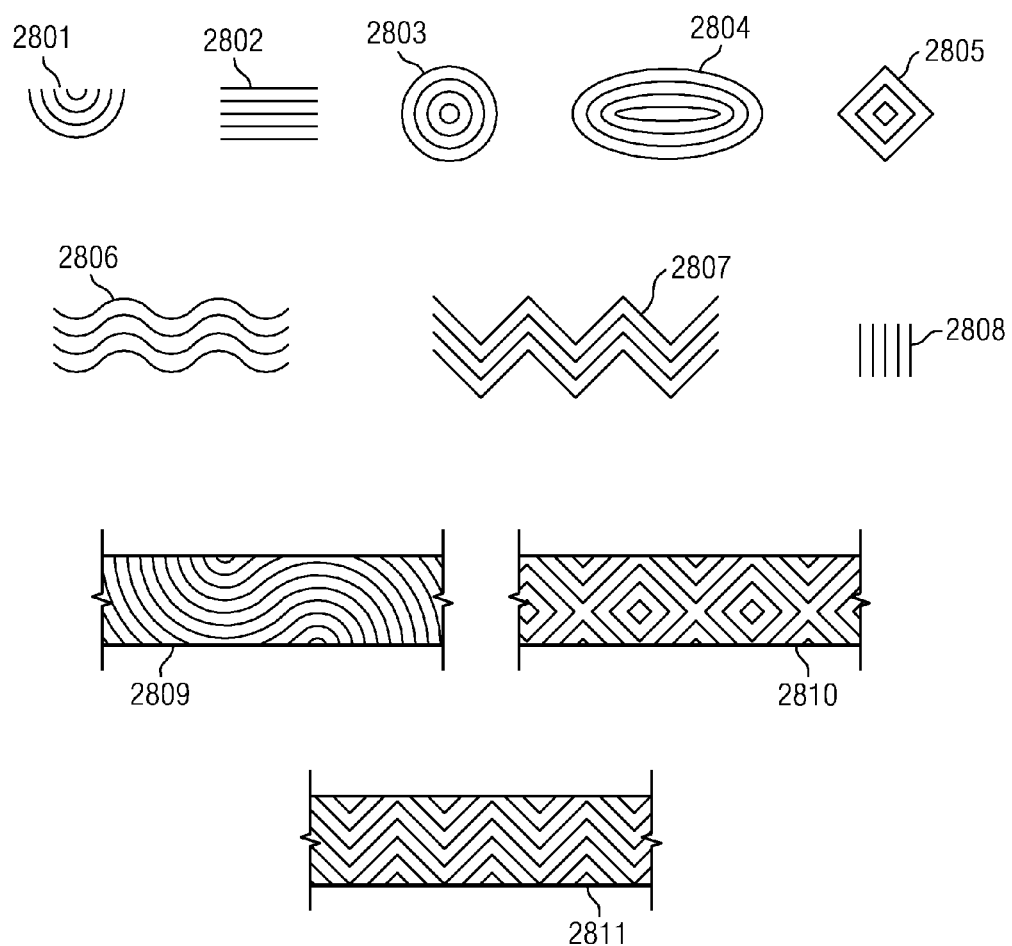
FIG. 28 includes illustrations of various geometric pattern designs for padding.
Figure 28B:
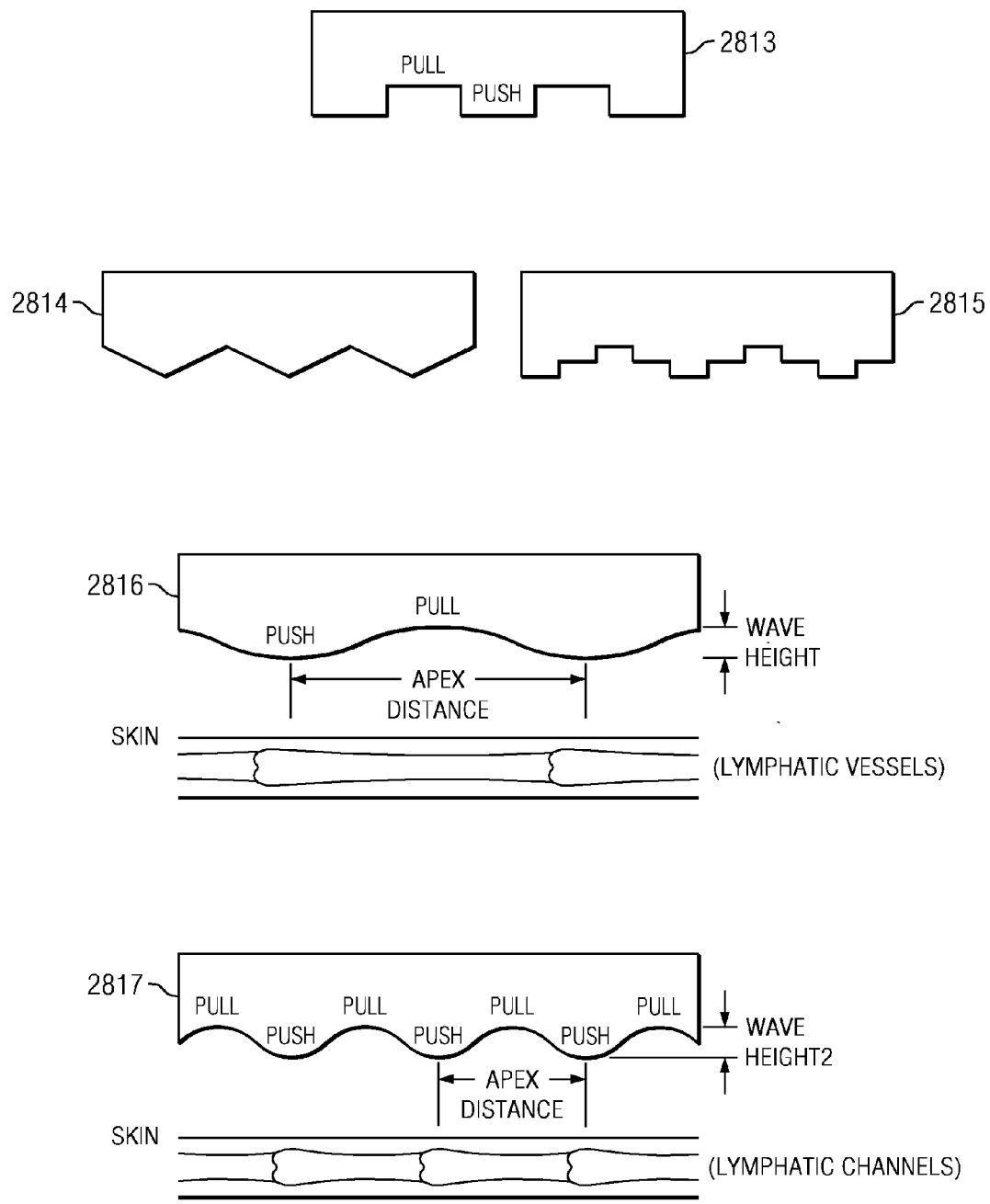

Another important aspect of this novel material for use in or with a compression device is the variation in thickness of the material. The material may in some embodiments have variations of thicknesses with a geometrical or wave-like pattern. These variations of thickness would effectively augment a push-pull mechanism on the underlying skin. The space between these waves and depth of these waves would vary. These waves would be 4 mm to 5 cm linear distance from apex to apex of the wave with a wave height of 1 mm to 1 cm, although larger heights and shorter or longer linear distances between apexes are possible. These waves in the material height may be perpendicular to the length of the finger-like projections, or may be asymmetrical. The waves/geometric patterns may all be symmetrical in length and height or may be asymmetrical. Certain material thickness and patterns may be advantageous over certain body areas, and any combinations may be used to get the desired effect. FIGS. 28a and 28b show geometrical shapes 2801-2805 as well as waves 2806. These waves 2806 are shown only on one side of the material, but it is understood the geometrical patterns may be on one or both sides of the material for added effect, enhanced breathability, reduced material costs, and reduced cost of manufacture. Additionally, the waves or geometrical shapes may be on the side of the padding that goes against the skin, or for more subtle effect may go on the side away from the skin, so that the overlying compression provides the effect. The side going toward the skin may or may not have an adhesive layer to attach to the skin.

The material utilized may have different tensile strength and different degrees of elongation. Since the material will be placed next to the skin, it will need some stretch to work well over joint areas. The material may have 110% to 300% maximal elongation with ideal elongation around 125-160% and good recoil. The material chosen may have variation in its tensile strength, such that once applied to a stretched skin area it can retract with some force, creating buckling which will push and pull against lymphatics. It is important to realize that the wave shape of the material can create this buckling and stretching of the underlying skin. By using a coating on the selected material which has high coefficient of friction against the skin, this can augment the push pull of the skin.

Accordingly, the present disclosure provides a material which can be used as a stand alone product under compression attached to a compression device in order to facilitate flow of blood and lymph through the skin and underlying tissues. This material may consist of a foam or spacer fabric in the preferred embodiments, although other embodiments may be created from neoprene, breathoprene, or gel polymer or other materials. The material may or may not have laminated fabric on one or both sides. The material may or may not have an adhesive tape backing to attach it to the skin. This adhesive coating may or may not be applied with a geometric or other pattern such that it is applied selectively to parts of the material for better performance and breathability. For instance, it may be advisable to have adhesive on just the troughs of the wave or just the crests of the wave when a wave type microgeometry design is utilized. The material may have X-shaped, Y-shaped, or fan-like projections which may vary in length. Long finger-like projections may interconnect one fan-like base to a second fan-like base. The finger-like projections may be straight or wavy and may have branching. The finger-like projections may be symmetrical or asymmetrical. The material may have variations in thickness with a wave or geometric pattern. The thickness may vary 0.1-1 cm in these patterned areas. If waves are used, these may run approximately perpendicular to the length of the finger-like projections in order to push and pull on the underlying skin. The waves may have distances between apexes of 4 mm-5 cm linear distance and wave height of 1 mm-9 mm, although thicker material and heights are possible. The material will have some elongation and some tensile strength, with maximal elongation of 110%-300%, with preferred elongation in the 125-160% range. The tension on the elongated material may vary, and several versions of the product may be developed with different tensions, in order to provide different degrees of push-pull on the underlying skin. The material chosen may have coefficient of friction on the skin which is high, or have a coating with high coefficient of friction on the skin, such that it is not uncomfortable or irritating, but effectively pushes and pulls on the skin during movement to facilitate blood and fluid flow through the skin and underlying tissues.

The invention details a planar compression material which can be trimmed to create appendages. The planar compression material in the preferred embodiment is a short-stretch material, but it can in other embodiments, nonelastic, medium stretch, or high stretch material. In the preferred embodiment the material is a short-stretch material with 15-90% maximal stretch, and with abrupt end-stretch or bandage lock-out so that it will not stretch further. This enables the user to know when the material quits stretching, and gives a baseline resting compression level for the material. The compression material can be engineered so that properly trimmed garments can provide resting compression levels of 8-15 mmHg, 15-20 mmHg, 20-30 mmHg, or 30-40 mmHg. Use of other compression ranges such as the German Raul scale or other scales are possible. The resting compression level is the compression level when the patient is supine and the garment is properly applied. It is understood that a garment applied at end-stretch will have a dynamic compression response depending the patients position. Sitting will increase the compression some, and standing will increase the compression level even further. Application of a short-stretch material over a muscle area will create large spikes in pressure when the muscle activates, such as is commonly seen with the calf muscle pump.

The invention may have trim lines or markings indicating where to cut the material. These trim lines may create rectangular, band-like, trapezoidal, curved, or triangular appendages in order to provide appropriate therapeutic compression to a body portion. Typically these trim lines will follow paths perpendicular to the underlying limb portion, but the trim lines may be angled more upward in order to lift and compress lobules, or angled downward for increased comfort or relaxation of a body portion. Varying the width of the appendages can alter the compression vector force applied to the underlying body member. Thus, the trim lines can be utilized to create a gradient flow of compression by creating narrow appendages distally and wider appendages proximally. Placement of trim lines with a compressed scale can create a simpler more therapeutic level of compression by considering circumference of the limb, elongation of the material, and compressive force of the material when stretched. Use of extra compressive material can improve lift and compression to problematic areas of the patient, or to ensure better fit and function of the garment.

In some aspects, the present disclosure is directed to garment for providing one or more large areas of compression material with indicia and markings that allow trimming of the garment. The compression materials may be non-elastic, short-stretch elastic, moderate-stretch, or high-stretch construction.

In different exemplary aspects, the garment may include regions where additional compression materials may be added to provide higher compression, for example, over lobules.

In different exemplary aspects, the garment may include areas where low profile padding may be attached to the garment using permanent, semi-permanent, removable, or selectively attachable mechanisms.

In other exemplary aspects, this garment material may include one or more layers of spacer fabric to provide padding, reduce fibrotic areas, or channel lymph flow to patient areas.

In different exemplary aspects the padding may beveled at edges providing a transition in thickness from the second region to the first region. The body portion may comprise a pocket and the second region may be formed of a selectively removable pad insertable into the pocket. The second region may comprise a plurality of regions having different padding thicknesses. The tibia includes 0.2 cm padding and the anterior ankle portion includes 0.8 cm padding. The padding in the second region is about 0.1-0.2 cm thick. The second region comprises a padded material permanently fixed to the tubular body portion. The garment may have a length sufficient to extend from a patient's foot to a patient's thigh. The second region is formed of a laminate of a plurality of padding pieces. The second region comprises a narrow spacing between adjacent padding pieces, the narrow spacing being disposed on the liner to overlie the anterior tibial crest and to distribute compression loading to the either side. The second region covers the anterior ankle and comprises a plurality of slits or grooves extending laterally across a central portion of the second region. The second region comprises a plurality of channels formed as indentations in the second region. The second region is arranged in the body portion to cover an anterior ankle region, a malleoli region, and a tibia region of the limb. This padded area may be selectively detachable or permanently attached to the compression garment.

In some aspects, the present disclosure is directed to a low profile garment for providing increased comfort to a patient's limb during treatment with a compression garment by distributing subbandage pressure at bony areas of the limb. The garment including a first region having relatively less padding and a second region having relatively more padding, the second region being located on the body portion to align with relatively harder tissue areas of the limb, the first region being located on the body to align with relatively softer tissue areas of the limb, the body portion having a beveled edge portion transitioning from the second region to the first region.

In some aspects, the present disclosure is directed to a system for applying therapeutic pressure to a patient's limb. The system comprises: an optional liner with or without padded areas on the liner, the liner comprising a tubular body portion having a proximal opening for receiving a limb and being sized to extend about the circumference of the limb. The system also comprises a compression garment consisting of large geographical shapes of compression material, the compression material having an attachment mechanism for interconnecting the compression material to the limb. The compression material may include trimmable appendages to which the attachment mechanism will interconnect the garment materials in a circular fashion about the limb section. The garment may consist of a proximal and distal section and a jointpiece.

In some aspects, the present disclosure is directed to a method of treating a condition of a patient's limb. It comprises: applying a compression garment with a large geographical sheet of compression material. The compression material may consist of short-stretch material. The method also comprises aligning the garment and attachment mechanisms in order to apply a therapeutic range of compression to the limb.

Some aspects of embodiments of the invention include 1) planar short-stretch compression material; 2) planar compression material with trim-to-fit concept (cover nonelastic, short-stretch, elastic embodiments); 3) planar compression material with spacer fabric padding; and 4) indicia system for setting correct compression level, etc.

Some aspects of the invention include a customizable therapeutic compression apparatus for treating a condition comprising a sheet of flexible and stretchable material having an inner surface configured for positioning proximate to a body portion, wherein the sheet is configured to apply varying amounts of therapeutic compression to the body portion based on an amount of stretch provided to the sheet; at least first and second indicia identifying first and second locations, respectively, to be trimmed to achieve first and second amounts of therapeutic compression, respectively, wherein the sheet is configured to conform to a shape of the body portion after being trimmed based on either of the first and second indicia; and an attachment mechanism configured to couple a first side of the sheet with a second side of the sheet to restrain the sheet about the body portion with an amount of compression indicated by one of the first and second indicia. The sheet may comprise a short-stretch material with a maximum stretch in a range from 15% to 90% and with a resting compression level when the short-stretch material is applied at or near end-stretch. The resting compression level may be within a range of 8-15 mmHg. The resting compression level may be within a range of 15-20 mmHg. The resting compression level may be within a range of 20-30 mmHg. The resting compression level may be within a range of 30-40 mmHg. The sheet may comprise a substantially non-elastic material. The sheet may comprise one of a medium-stretch and a high-stretch material. The apparatus may further comprise at least one appendage coupled to the sheet, wherein the at least one appendage includes at least a portion of the attachment mechanism and is configured to secure the sheet about the body portion. The sheet may further comprise at least a third indicium identifying a third location to be trimmed to create the appendage from the material forming the sheet. The apparatus may further comprise at least a third indicium identifying a third location to be trimmed to modify the sheet in order to conform to the shape of the body portion. The apparatus may further comprise at least a third indicium identifying a portion of the sheet to be removed to form an aperture in the sheet that does not intersect an edge of the sheet. The first and second indicia may be color coded. The sheet may include at least one band, and wherein at least one of the first and second indicia is configured to modify a characteristic of the band when trimmed. The characteristic may be one of a shape of the band, a length of the band, and a width of the band. The apparatus may further comprise at least third and fourth indicia identifying locations on the apparatus corresponding to varying levels of compression when the sheet is stretched. At least one of the first and second indicia may represent a compressed scale configured to provide cutting of the compression apparatus in an unstretched position. The apparatus may further comprise a padding layer positioned between the inner surface and the body portion. The padding layer may provide a ribbed configuration with channels formed between longitudinal raised areas. The padding layer may provide a waffled configuration with channels defined by raised areas that are isolated from one another, wherein at least some of the raised areas are surrounded by channels. The raised areas may be pyramid shaped. The raised areas may be square shaped. The raised areas may be tapered. The apparatus may further comprise a pocket positioned on the inner surface, wherein the padding layer is removably positioned within the pocket. The apparatus may further comprise a plurality of finger-like projections coupled to the inner surface, wherein the finger-like projections extend away from a central location. The finger-like projections may be semi-rigid and configured to be at least partially compressed between the inner surface and the body portion. The finger-like projections may be at least partially covered with an adhesive. The apparatus may further comprise a joint piece configured for positioning over a joint of the body member. The sheet may be positioned on opposite sides of the joint piece. A first portion of the sheet may be characterized by a one-way stretch material and a second portion of the sheet is characterized by a two-way stretch material.

Some aspects of the invention include a planar sheet configured for form-fitting a limb hull and providing desired compression vectors to each of a plurality of areas of the limb hull, comprising at least one rived portion having a predetermined length, shape, and direction that is based on at least one physical measurement of the limb hull, wherein creation of the rived portion alters the planar sheet from an initial state; and at least one pre-set limit for stretching at least one selected area of the planar sheet for form-fitting to the limb hull and to provide a desired compression vector to at least one area of the limb hull. The rived portion may be identified by visible indicia when the planar sheet is in the initial state. The planar sheet may further comprise a channeled spacer layer.

Some aspects of the invention may include a method for providing for the selection of a customizable therapeutic compression apparatus for treating a condition comprising identifying an amount of stretch at which the compression apparatus is to be applied to a body portion; calculating a plurality of compression values for the compression apparatus, wherein each of the plurality of compression values corresponds to a predetermined compression level relative to the body portion for one of a plurality of measurements of the body portion at the identified amount of stretch; and providing a user readable display of the plurality of compression values, wherein the user is able to view the display to select the compression apparatus based upon a measurement of the body portion to be compressed and a desired compression level. The user readable display may be a graph having a first axis displaying a plurality of the compression levels and a second axis displaying the plurality of measurements of the body portion, and wherein the plurality of compression values are charted against the first and second axes. The method may further comprise providing a plurality of sets of compression values, wherein each set of compression values represents a different compression apparatus. The method may further comprise providing a plurality of sets of compression values corresponding to a single compression apparatus, wherein each set of compression values represents a different percentage of maximal stretch of the single compression apparatus. Each predetermined compression level may represent a resting compression level. Each of the plurality of measurements of the body portion may be circumferential measurements. Each predetermined compression level may be a subbandage pressure level. Each predetermined compression level may be a skin surface pressure level.

Some aspects of the invention may include a device comprising a material layer having a compressed scale reproduced thereon for use with a customizable therapeutic compression apparatus adapted to provide compression to a body portion, the compressed scale having an indicator representing a location on the compression apparatus to be cut when the compression apparatus is in an unstretched position in order to achieve a desired compression level when the compression apparatus is stretched to a defined amount of stretch, wherein the indicator visually corresponds to a user measurement of the body portion taken using an actual scale but represents a compressed scale rather than the actual scale, and wherein the indicator is positioned relative to physical dimensions of the compression apparatus based on the compressed scale so that cutting at the location physically alters the compression apparatus so as to provide the desired compression level. The compressed scale may be calculated based on $BLn=((LMa+PL)/(1+BSA))*(1+PBOd)$, where $BLn$ is a band length of the compression apparatus needed for a selected limb level of the body portion, $LMa$ is the actual measurement for the limb, $BSA$ is the percent band stretch at application, $PBOd$ is the percent band overlap desired, and $PL$ is the circumference of a padded liner at that limb level. The device may be a ruler. The device may be the compression apparatus.

Some aspects of the invention may include a method of manufacturing a garment for treating a medical condition on a patient, comprising determining a first level of compression applied to a limb by a garment extending about the limb, the garment being formed of a single sheet of trimmable, flexible and stretchable material shaped and arranged to extend about a limb and apply therapeutic compression to the limb, the garment having appendages sized with a first width; determining a second level of compression applied to a limb by a garment extending about the limb, the garment having appendages sized with a first width; applying indicia on the garment that identifies the appendages with the first width; applying indicia on the garment that identifies the appendages with the second width; providing instructions for a user to trim the appendage at the first width when the limb is sized at a first diameter; and providing instructions for the user to trim the appendage at the second width when the limb is sized at a second diameter less than the first diameter.

Some aspects of the invention may include an apparatus for facilitating fluid flow in and under a skin layer of a body portion comprising a sheet of flexible material capable of elongation and having an inner surface configured for positioning proximate to the skin layer; and a plurality of extensions formed in the sheet, wherein at least some of the plurality of extensions extend from a central location, and wherein the plurality of extensions are geometrically configured to provide channeling of lymphatic flow. The apparatus may further comprise a compression garment, wherein the sheet is positioned between the compression garment and the skin layer. The sheet may be affixed to the compression garment. The sheet may be formed as part of the compression garment. At least a portion of the extensions may have a patterned side that is positioned facing the skin, wherein the patterned side of each extension includes raised areas relative to other portions of the patterned side of the extension. The patterned side may include channeling formed by raised areas that are pyramidal in shape. The patterned side may include channeling formed by raised areas that are square in shape. The patterned side may include channeling formed by wave-like raised areas. The wave-like raised areas may be geometrically arranged based on a shape of the body portion over which the extension is to be positioned. At least some of the plurality of extensions may be coated with an adhesive material to adhere to the skin layer. The extensions may be arranged in a fan shape and may fan out from the single location. The extensions may be arranged in an X shape. The extensions may be coupled to one another proximally and distally and gaps may exist between the extensions between the proximal and distal couplings.

It is noted that the use of directional terms herein, such as upper, lower, lateral, and others are merely exemplary, and may encompass other directions, such as the device being on its side, unless so indicated. Although several selected embodiments have been illustrated and described in detail, it will be understood that they are exemplary, and that a variety of substitutions and alterations are possible without departing from the spirit and scope of the present invention, as defined by the following claims.

We claim:

1. A customizable therapeutic compression apparatus for treating a condition, the apparatus comprising:
   a sheet of flexible and stretchable material having an inner surface to be positioned proximate a limb of a patient;
   the sheet having a length and a width;
   the sheet configured to apply varying amounts of therapeutic compression to the limb based on an amount of stretch provided to the sheet;
   at least one marking showing where to trim the sheet to shorten the length to fit a shorter limb;
   numbered markings showing where to trim the width of the sheet to fit a limb or limb portion of corresponding circumference;
   the numbered markings providing a compressed scale taking into account an intended overlap when the sheet is wrapped about a limb; and
   at least one attachment mechanism configured to couple a first side of the sheet with a second side of the sheet to restrain the sheet about a limb.

2. The apparatus of claim 1 wherein the sheet comprises a short-stretch material with a maximum stretch in a range from 15% to 90% and with a resting compression level when the short-stretch material is applied at or near end-stretch.

3. The apparatus of claim 2 wherein the resting compression level is within a range of 15-20 mmHg.

4. The apparatus of claim 2 wherein the resting compression level is within a range of 20-30 mmHg.

5. The apparatus of claim 2 wherein the resting compression level is within a range of 30-40 mmHg.

6. The apparatus of claim 1 wherein the compressed scale further takes into account an intended stretch of the sheet when the sheet is wrapped about a limb with the intended overlap.

7. The apparatus of claim 1 wherein the sheet comprises one of a medium-stretch and a high-stretch material.

8. The apparatus of claim 1 wherein the at least one marking comprises a number showing where to trim the length of the sheet to fit a limb of corresponding length.

9. The apparatus of claim 8 wherein the at least one marking and the number thereof provide a one-to-one scale.

10. The apparatus of claim 1 further comprising at least one indicia identifying a location to be trimmed to modify the sheet in order to conform to a shape of a limb.

11. The apparatus of claim 10 wherein the at least one indicia identifies a portion of the sheet to be removed to form an aperture in the sheet that does not intersect an edge of the sheet.

12. The apparatus of claim 10 wherein the at least indicia identifies at least one location to cut the sheet to form at least one tab along one side of the sheet.

13. The apparatus of claim 12 wherein an attachment mechanism of the at least one attachment mechanism engages each tab of the at least one tab.

14. The apparatus of claim 1 wherein the sheet is substantially continuous.

15. The apparatus of claim 1 wherein the at least one marking and the number markings are applied to the sheet or to a guide pattern accompanying the sheet.

16. The apparatus of claim 1 further comprising a padding layer providing a ribbed configuration with channels formed between longitudinal raised areas.

17. The apparatus of claim 1 further comprising a padding layer providing a waffled configuration with channels defined by raised areas that are isolated from one another, wherein at least some of the raised areas are surrounded by channels.

18. The apparatus of claim 1 further comprising a plurality of finger-like projections coupled to the inner surface, wherein the finger-like projections extend away from a central location.

19. The apparatus of claim 18 wherein the finger-like projections are semi-rigid and configured to be at least partially compressed between the inner surface and a limb of a patient.

20. The apparatus of claim 18 wherein the finger-like projections are at least partially covered with an adhesive.

21. A customizable therapeutic compression apparatus for treating a condition, the apparatus comprising:
- a sheet of flexible and stretchable material having an inner surface to be positioned proximate a body portion of a patient;
- the sheet having a length and a width;
- the sheet configured to apply varying amounts of therapeutic compression to a body portion based on an amount of stretch provided to the sheet;
- at least one marking showing where to trim the sheet to shorten the length to fit a shorter body portion;
- numbered markings showing where to trim the width of the sheet to fit a body portion of corresponding circumference;
- the numbered markings providing a compressed scale taking into account an intended overlap when the sheet is wrapped about a body portion; and
- at least one attachment mechanism configured to couple a first side of the sheet with a second side of the sheet to retain the sheet about a body portion.

22. The apparatus of claim 21 wherein the compressed scale further takes into account an intended stretch of the sheet when the sheet is wrapped about a body portion with the intended overlap.

23. A customizable therapeutic compression apparatus for treating a condition, the apparatus comprising:
- a sheet of flexible and stretchable material having an inner surface to be positioned proximate a body portion of a patient;
- the sheet having a length and a width;
- the sheet configured to apply varying amounts of therapeutic compression to a body portion based on an amount of stretch provided to the sheet;
- at least one marking showing where to trim the sheet to shorten the length to fit a shorter body portion;
- numbered markings showing where to trim the width of the sheet to fit a body portion of corresponding circumference;
- the numbered markings providing a compressed scale taking into account an intended stretch of the sheet when the sheet is wrapped about a body portion; and
- at least one attachment mechanism configured to couple a first side of the sheet with a second side of the sheet to retain the sheet about a body portion.

* * * * *